US012005097B2

(12) United States Patent
Kerwin et al.

(10) Patent No.: US 12,005,097 B2
(45) Date of Patent: Jun. 11, 2024

(54) AFLIBERCEPT FORMULATIONS AND USES THEREOF

(71) Applicant: Just-Evotec Biologics, Inc., Seattle, WA (US)

(72) Inventors: Bruce A. Kerwin, Bainbridge Island, WA (US); Julee A. Floyd, Seattle, WA (US); Alison J. Gillespie, Seattle, WA (US); Christine C Siska, Seattle, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 232 days.

(21) Appl. No.: 17/492,649

(22) Filed: Oct. 3, 2021

(65) Prior Publication Data

US 2022/0016210 A1   Jan. 20, 2022

Related U.S. Application Data

(63) Continuation of application No. 16/462,527, filed as application No. PCT/US2017/062521 on Nov. 20, 2017, now Pat. No. 11,135,266.

(60) Provisional application No. 62/497,584, filed on Nov. 21, 2016.

(51) Int. Cl.
| | | |
|---|---|---|
| *A61K 38/17* | (2006.01) | |
| *A61K 9/00* | (2006.01) | |
| *A61K 47/02* | (2006.01) | |
| *A61K 47/10* | (2017.01) | |
| *A61K 47/12* | (2006.01) | |
| *A61K 47/18* | (2017.01) | |
| *A61K 47/22* | (2006.01) | |
| *A61K 47/26* | (2006.01) | |
| *A61K 47/34* | (2017.01) | |

(52) U.S. Cl.
CPC .......... *A61K 38/179* (2013.01); *A61K 9/0019* (2013.01); *A61K 9/0048* (2013.01); *A61K 47/02* (2013.01); *A61K 47/10* (2013.01); *A61K 47/12* (2013.01); *A61K 47/183* (2013.01); *A61K 47/22* (2013.01); *A61K 47/26* (2013.01); *A61K 47/34* (2013.01)

(58) Field of Classification Search
None
See application file for complete search history.

(56) References Cited

U.S. PATENT DOCUMENTS

| | | |
|---|---|---|
| 7,070,959 B1 | 7/2006 | Papadopoulos et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| 7,374,757 B2 | 5/2008 | Papadopoulos et al. |
| 7,374,758 B2 | 5/2008 | Papadopoulos et al. |
| 7,521,049 B2 | 4/2009 | Wiegand et al. |
| 7,524,499 B2 | 4/2009 | Papadopoulos et al. |
| 8,029,791 B2 | 10/2011 | Papadopoulos et al. |
| 8,092,803 B2 | 1/2012 | Furfine et al. |
| 8,110,546 B2 | 2/2012 | Dix et al. |
| 8,133,863 B2 | 3/2012 | Maggio |
| 8,343,737 B2 | 1/2013 | Papadopoulos et al. |
| 8,372,396 B2 | 2/2013 | Andya et al. |
| 8,404,638 B2 | 3/2013 | Dix et al. |
| 8,647,842 B2 | 2/2014 | Papadopoulos et al. |
| 8,710,004 B2 | 4/2014 | Dix et al. |
| 8,921,316 B2 | 12/2014 | Dix et al. |
| 9,139,644 B2 | 9/2015 | Papadopoulos et al. |
| 9,254,338 B2 | 2/2016 | Yancopoulos |
| 9,364,542 B2 | 6/2016 | Chang |
| 9,416,167 B2 | 8/2016 | Dix et al. |
| 9,511,140 B2 | 12/2016 | Dix et al. |
| 9,580,489 B2 | 2/2017 | Furfine et al. |
| 9,636,400 B2 | 5/2017 | Dix et al. |
| 9,669,069 B2 | 6/2017 | Yancopoulos |
| 9,708,386 B2 | 7/2017 | Papadopoulos et al. |
| 9,982,032 B2 | 5/2018 | Park et al. |
| 10,130,681 B2 | 11/2018 | Yancopoulos |
| 2005/0158316 A1 | 7/2005 | Lam et al. |
| 2010/0015157 A1 | 1/2010 | Andya et al. |
| 2013/0323788 A1 | 12/2013 | Chen et al. |
| 2014/0127227 A1 | 5/2014 | Chang |
| 2015/0079087 A1 | 3/2015 | Dix et al. |
| 2016/0101152 A1 | 4/2016 | Yancopoulos |
| 2016/0244504 A1 | 8/2016 | Dix et al. |
| 2016/0251411 A1 | 9/2016 | Burakov et al. |
| 2016/0271253 A1 | 9/2016 | Chang |
| 2016/0376342 A1 | 12/2016 | Park et al. |

(Continued)

FOREIGN PATENT DOCUMENTS

| | | |
|---|---|---|
| CN | 101478949 A | 7/2009 |
| EP | 1183353 B1 | 3/2002 |
| EP | 1544299 B1 | 6/2005 |

(Continued)

OTHER PUBLICATIONS

Robert J. Falconer et al., "Stabilization of a monoclonal antibody during purification and formulation by addition of basic amino acid excipients," J. Chem Technol. Biotechnol. 2011; 86:942-948, published Jun. 7, 2011.

Lauren Platts et al., "Control of Globular Protein Thermal Stability in Aqueous Formulations by the Positively Charge Amino Acid Excipients," Journal of Pharmaceutical Sciences 105 (2016) 3532-3536, Elsevier Inc.

European Patent Office, "Notification of Transmittal of the International Search Report and the Written Opinion of the International Searching Authority, or the Declaration, ISR and Written Opinion of the ISA" Feb. 5, 2018 (May 2, 2018).

(Continued)

*Primary Examiner* — Christine J Saoud
*Assistant Examiner* — Jon M Lockard
(74) *Attorney, Agent, or Firm* — Law Offices of Nisan Steinberg

(57) ABSTRACT

Ophthalmic formulations comprising aflibercept are disclosed that are suitable for a method of treatment of an eye disorder or disease by intravitreal or topical administration.

18 Claims, 13 Drawing Sheets

Specification includes a Sequence Listing.

(56) References Cited

U.S. PATENT DOCUMENTS

2017/0045527 A1   2/2017   Muthusamy et al.
2017/0360930 A1   12/2017   Dix et al.

FOREIGN PATENT DOCUMENTS

| EP | 1861116 | B1 | 12/2007 |
| EP | 2364691 | B1 | 9/2011 |
| EP | 2586459 | B1 | 5/2013 |
| WO | 2005000895 | A2 | 1/2005 |
| WO | 2006044908 | A2 | 4/2006 |
| WO | 2006104852 | A2 | 10/2006 |
| WO | 2007149334 | A2 | 12/2007 |
| WO | 2013181495 | A2 | 12/2013 |
| WO | 2016087677 | A1 | 6/2016 |
| WO | 2016208989 | A1 | 12/2016 |
| WO | 2017046140 | A1 | 3/2017 |
| WO | 2017129685 | A1 | 8/2017 |
| WO | 2018094316 | A1 | 5/2018 |
| WO | 2019099965 | A1 | 5/2019 |

OTHER PUBLICATIONS

Transmittal and International Preliminary Report on Patentability (IPRP) in PCT/US2017/062521, International Bureau of WIPO, dated May 21, 2019 (dated May 31, 2019).
EPO Communication pursuant to Rule 161(1) and 162 EPC in corresponding EP17808289.7, dated Jun. 28, 2019.
Rogers, Richard S et al., "Development of a quantitative mass spectrometry multi-attribute method for characterization, quality control testing and disposition of biologics," mAbs 7:5, 881-890; Sep./Oct. 2015.
JPO Office Action re corresponding Japanese National Phase Appln. JP 2019-526570 (dated Apr. 20, 2021) with English translation.
CNIPA Office Action re corresponding Chinese National Phase Appln. CN 201780069882.9 (dated Jan. 29, 2021) with English translation.
CNIPA 2d Office Action in CN201780069882.9, corresponding national phase of PCT/US2017/062521, with English translation (dated Oct. 27, 2021).
JPO 2d Office Action in JP2019-526570, corresponding national phase of PCT/US2017/062521, with English translation (dated Dec. 1, 2021).
EPO Office Action in EP17808289.7, corresponding national phase of PCT/US2017/062521 (dated Jun. 15, 2022).
JPO Decision to Grant in JP2019-526570, corresponding national phase of PCT/US2017/062521 (dated Jun. 29, 2022).
CNIPA Decision to Grant in CN201780069882.9, corresponding national phase of PCT/US2017/062521, with English translation (dated Jul. 11, 2022).

AFLIBERCEPT FORMULATIONS AND USES THEREOF

This is a continuation of U.S. patent application Ser. No. 16/462,527, which issued as U.S. Pat. No. 11,135,266 B2 on Oct. 5, 2021, and which was filed under 35 U.S.C. § 371, on May 20, 2019, which was a U.S. national phase application under 35 U.S.C. § 371 of United States Patent Cooperation Treaty Application No. PCT/US2017/062521, filed Nov. 20, 2017, which claims priority from U.S. Provisional Patent Application Ser. No. 62/497,584, filed in the United States Patent and Trademark Office on Nov. 21, 2016, all of which applications are incorporated by reference in their entireties herein.

SEQUENCE LISTING

The instant application contains a Sequence Listing which has been filed electronically in ASCII format and is hereby incorporated by reference in its entirety. Said ASCII copy, created on Sep. 26, 2021, is named JUST0271_SL.txt and is 4,093 bytes in size.

BACKGROUND OF THE INVENTION

1. Field of the Invention

This invention relates to pharmaceutical formulations of aflibercept fusion protein suitable for ophthalmic administration.

2. Discussion of the Related Art

Aflibercept is a recombinant fusion protein that includes two main components: the vascular endothelial growth factor (VEGF) binding portions from the extracellular domains of human VEGF receptors 1 and 2, fused to the Fc portion of human IgG1. (See, Papadopoulos et al., *Modified chimeric polypeptides with improved pharmacokinetic properties*, WO 00/75319 A1; U.S. Pat. No. 7,070,959B2). Structurally, aflibercept is a dimeric glycoprotein with a protein molecular weight of about 96.9 kilo Daltons (kDa). It contains approximately 15% glycosylation to give a total molecular weight of approximately 115 kDa. All five putative N-glycosylation sites on each polypeptide chain predicted by the primary sequence can be occupied with carbohydrate and exhibit some degree of chain heterogeneity, including heterogeneity in terminal sialic acid residues.

The United States Food and Drug Administration (FDA) approved aflibercept for marketing in November 2011, and the European Medicines Agency (EMA) approved in November 2012.

Aflibercept, under the brand name Eylea® (Regeneron Pharmaceuticals, Inc.) is used as an ophthalmic agent in the treatment of eye disorders or diseases, e.g., macular edema following Central Retinal Vein Occlusion (CRVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD).

Ziv-aflibercept, under the brand name Zaltrap® (Regeneron Pharmaceuticals, Inc.), was developed as an injection for treatment of metastatic colorectal cancer.

Known formulations for aflibercept include those described by Furfine et al. (Furfine et al., VEGF antagonist formulations for intravitreal administration, U.S. Pat. Nos. 8,092,803; 9,580,489; EP 2364691B1; WO2007149334A2) and by Dix et al. (Dix et al., VEGF Antagonist Formulations, WO2006104852 A2; U.S. Pat. Nos. 8,921,316; 9,636,400).

There is still a need for formulations of aflibercept with enhanced stability, which the present invention provides.

SUMMARY OF THE INVENTION

The present invention relates to an ophthalmic formulation of aflibercept, which formulation includes: (a) aflibercept in a concentration of 5-100 mg/mL; (b) a buffer at 5-50 mM concentration; (c) a non-ionic surfactant; (d) a tonicifying agent selected from the group consisting of a polyol and an amino acid, or in some embodiments both a polyol and an amino acid, with the formulation having a final osmolality of about 300 mOsm/kg (i.e., 300±50 mOsm/kg). The concentration of chloride anion ($Cl^-$) in the inventive ophthalmic formulation is less than about 10 mM, and in some embodiments less than about 5 mM or less than about 1 mM; and the pH of the formulation is about pH 5.0 to about pH 6.5. The inventive ophthalmic formulation is suitable for intravitreal or topical administration. The inventive aflibercept-containing ophthalmic formulations have stability characteristics, e.g., significantly reduced aggregation over time, and visual characteristics as favorable, or more favorable, than other known ophthalmic formulations of aflibercept, for example, formulations containing added sodium chloride. Formulations of the invention can also be lyophilized and reconstituted, if desired.

The ophthalmic formulations of the present invention can be used as medicinal ophthalmic agents in a method of treatment of an eye disorder or disease, e.g., macular edema following Retinal Vein Occlusion (RVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD). Administration of the inventive ophthalmic formulation can be by intravitreal injection or, in some cases, by topical administration to the eye, as medically appropriate. The inventive formulations can be used for the treatment of these eye disorders or diseases and used in the preparation of medicaments for treatment of these eye disorders and diseases.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF EMBODIMENTS

Figure 1:
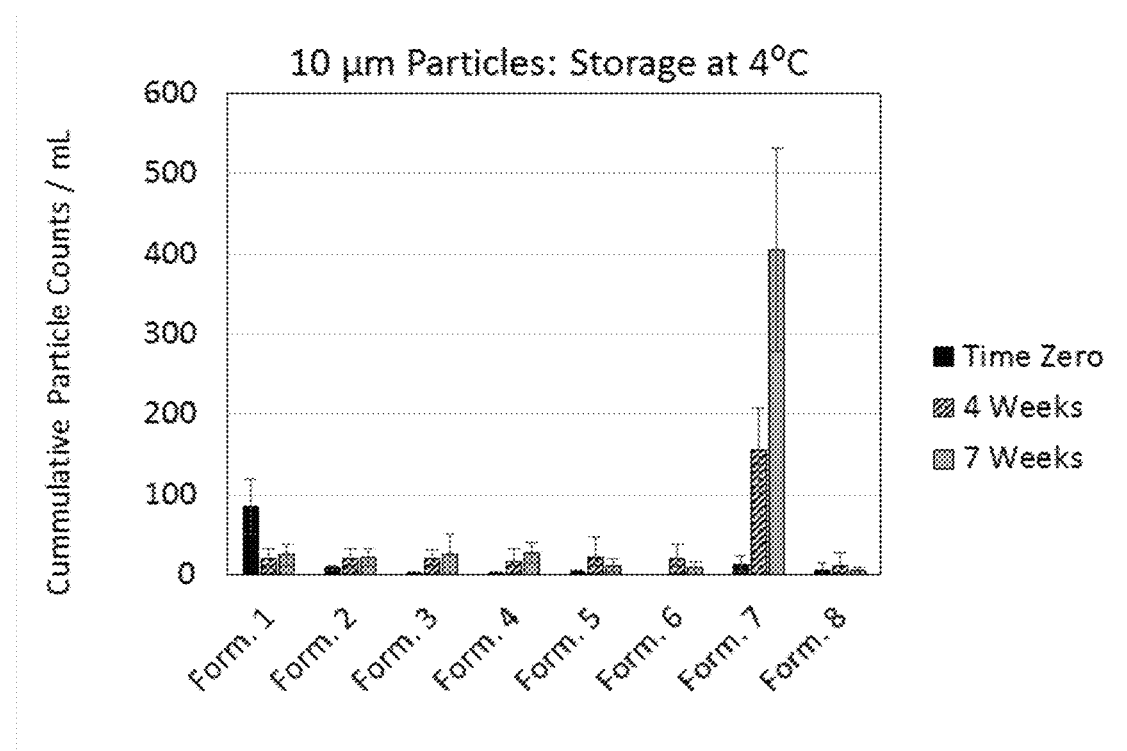
FIG. 1 shows results from subvisible particle analysis, conducted by small volume HIAC analysis. The 10-μm particle results showed that all samples had low levels of particles except Formulation 7, a formulation that exhibited increasing levels of particles during storage.

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

The present invention relates to an aqueous ophthalmic formulation, suitable for intravitreal or topical administration to a patient, which formulation includes aflibercept, which is also known commercially as Eylea®. Aflibercept is an assembly of two identical fusion polypeptide chains having the aflibercept amino acid sequence (SEQ ID NO:1), typically produced most conveniently by recombinant DNA expression technology. The aflibercept amino acid sequence is the following:

SEQ ID NO: 1
SDTGRPFVEMYSEIPEIIHMTEGRELVIPCRVTSPNITVTLKKFPLD

TLIPDGKRIIWDSRKGFIISNATYKEIGLLT<u>C</u>EATVNGHLYKTNYLT

HRQTNTIIDVVLSPSHGIELSVGEKLVLN<u>C</u>TARTELNVGIDFNWEYP

SSKHQHKKLVNRDLKTQSGSEMKKFLSTLTIDGVTRSDQGLYT<u>C</u>AAS

SGLMTKKNSTFVRVHEKDKTHT<u>C</u>PP<u>C</u>PAPELLGGPSVFLFPPKPKDT

LMISRTPEVT<u>C</u>VVVDVSHEDPEVKFNWYVDGVEVHNAKTKPREEQYN

STYRVVSVLTVLHQDWLNGKEYK<u>C</u>KVSNKALPAPIEKTISKAKGQPR

EPQVYTLPPSRDELTKNQVSLT<u>C</u>LVKGFYPSDIAVEWESNGQPENNY

KTTPPVLDSDGSFFLYSKLTVDKSRWQQGVNFS<u>C</u>SVMHEALHNHYTQ

KSLSLSPG//

Disulfide bridges are expected between the cysteine residues at following amino acid positions of SEQ ID NO:1 (underlined cysteine (C) residues shown in SEQ ID NO:1, above):
30-79 (intrachain)
124-185 (intrachain)
211-211 (interchain)
214-214 (interchain)
246-306 (intrachain)
352-410 (intrachain).

The two fusion polypeptide chains of aflibercept are covalently linked by disulfide linkage at amino acid positions 211 and 214 of SEQ ID NO:1. The fusion protein is typically glycosylated, with N-glycan covalently linked at asparagine residues at positions 36, 68, 123, 196, and 282 of SEQ ID NO:1 (bold/italicized asparagine (N) residues shown in SEQ ID NO:1 above). "Aflibercept" within the scope of the invention also includes embodiments in which one, both, or none, of the fusion polypeptide chains has the amino acid sequence SEQ ID NO:1 with an additional carboxy-terminal lysine (K) residue. The concentration of aflibercept in the inventive ophthalmic formulation is about 20 mg/mL to about 80 mg/mL, or about 30 mg/mL to about 50 mg/mL; for example, a concentration of about 40 mg/mL is useful in many embodiments of the formulation.

A "stable" formulation is one in which the protein therein essentially retains its physical stability and/or chemical stability and/or biological activity upon processing (e.g., ultrafiltration, diafiltration, other filtering steps, vial filling), transportation, and/or storage of the drug substance and/or drug product containing aflibercept. Together, the physical, chemical and biological stability of the protein in a formulation embody the "stability" of the protein formulation, e.g., the aflibercept formulation, which is specific to the conditions under which the formulated drug product (DP) is stored. For instance, a drug product stored at subzero temperatures would be expected to have no significant change in either chemical, physical or biological activity while a drug product stored at 40° C. would be expected to have changes in its physical, chemical and biological activity with the degree of change dependent on the time of storage for the drug substance or drug product. The configuration of the protein formulation can also influence the rate of change. For instance, aggregate formation is highly influenced by protein concentration with higher rates of aggregation observed with higher protein concentration. Excipients are also known to affect stability of the drug product with, for example, addition of salt increasing the rate of aggregation for some proteins while other excipients such as sucrose are known to decrease the rate of aggregation during storage. Instability is also greatly influenced by pH giving rise to both higher and lower rates of degradation depending on the type of modification and pH dependence.

Various analytical techniques for measuring protein stability are available in the art and are reviewed, e.g., in Wang, W. (1999), *Instability, stabilization and formulation of liquid protein pharmaceuticals*, Int J Pharm 185:129-188. Stability can be measured at a selected temperature for a selected time period. For rapid screening, for example, the formulation may be kept at 40° C. for 2 weeks to 1 month, at which time stability is measured. Where the formulation is to be stored at 2-8° C., generally the formulation should be stable at 30° C. for at least 1 month, or 40° C. for at least a week, and/or stable at 2-8° C. for at least two years.

A protein "retains its physical stability" in a pharmaceutical formulation if it shows minimal signs of changes to the secondary and/or tertiary structure (i.e., intrinsic structure), or aggregation, and/or precipitation and/or denaturation upon visual examination of color and/or clarity, or as measured by UV light scattering or by size exclusion high performance liquid chromatography, or other suitable methods. Physical instability of a protein, i.e., loss of physical stability, can be caused by oligomerization resulting in dimer and higher order aggregates, subvisible, and visible particle formation, and precipitation. The degree of physical degradation can be ascertained using varying techniques depending on the type of degradant of interest. Dimers and higher order soluble aggregates can be quantified using size exclusion chromatography, while subvisible particles may be quantified using light scattering, light obscuration or other suitable techniques. In one embodiment, the stability of the protein is determined according to the percentage of aflibercept monomer protein in the solution, with a low percentage of degraded (e.g., fragmented) and/or aggregated protein. An "aflibercept monomer" means an assembly of two polypeptide chains having the aflibercept amino acid sequence (SEQ ID NO:1), with or without an additional carboxy-terminal lysine residue on any of the polypeptide chains. In an "aflibercept monomer," the two aflibercept polypeptide chains are assembled through association and disulfide crosslinks of the immunoglobulin Fc domain portions of the sequences, as noted hereinabove. For example, an aqueous formulation comprising a stable protein may include (as a percentage of total protein) at least 95% aflibercept monomer, at least 96% aflibercept monomer, at least 97% aflibercept monomer, at least 98% aflibercept monomer, or at least 99% aflibercept monomer protein. Alternatively, an aqueous formulation of the invention may include (as a percentage of total protein) about 5% aggregate and/or degraded aflibercept protein.

A protein "retains its chemical stability" in a pharmaceutical formulation, if the chemical stability at a given time is such that covalent bonds are not made or broken, resulting in changes to the primary structure of the protein component, e.g., aflibercept. Changes to the primary structure may result in modifications of the secondary and/or tertiary and/or quaternary structure of the protein and may result in formation of aggregates or reversal of aggregates already formed. Typical chemical modifications can include isomerization, deamidation, N-terminal cyclization, backbone hydrolysis, methionine oxidation, tryptophan oxidation, histidine oxidation, beta-elimination, disulfide formation, disulfide scrambling, disulfide cleavage, and other changes resulting in changes to the primary structure including D-amino acid formation. Chemical instability, i.e., loss of chemical stability, may be interrogated by a variety of techniques including ion-exchange chromatography, capillary isoelectric focusing, analysis of peptide digests and multiple types of mass spectrometric techniques. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by charge-based methods, such as, but not limited to, ion-exchange chromatography, capillary isoelectric focusing, or peptide mapping.

Loss of physical and/or chemical stability may result in changes to biological activity as either an increase or decrease of a biological activity of interest, depending on the modification and the protein being modified. A protein "retains its biological activity" in a pharmaceutical formulation, if the biological activity of the protein at a given time is within about 30% of the biological activity exhibited at the time the pharmaceutical formulation was prepared. Activity is considered decreased if the activity is less than 70% of its starting value. Biological assays may include both in vivo and in vitro based assays such as ligand binding, potency, cell proliferation or other surrogate measure of its biopharmaceutical activity. As an example, biological activity of aflibercept can be estimated using an in vitro ligand binding assay such as inhibition of anti-placental growth factor binging to PGF by ELISA or human umbilical vein endothelial cell (HUVEC) proliferation assay.

Aflibercept for use in the invention is typically produced by recombinant expression technology. The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., *Molecular Cloning. A Laboratory Manual*. Cold Spring Harbor Laboratory, Cold Spring Harbor, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid. Recombinant DNA molecules useful in expressing aflibercept fusion protein are described, e.g., by Papadopoulos et al., Modified Chimeric Polypeptides with Improved Pharmacokinetic Properties, U.S. Pat. No. 7,070,959 B2; and WO 00/75319 A1).

The term "naturally occurring," where it occurs in the specification in connection with biological materials such as polypeptides, nucleic acids, host cells, and the like, refers to materials which are found in nature.

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

A "promoter" is a region of DNA including a site at which RNA polymerase binds to initiate transcription of messenger RNA by one or more downstream structural genes. Promoters are located near the transcription start sites of genes, on the same strand and upstream on the DNA (towards the 5' region of the sense strand). Promoters are typically about 100-1000 bp in length.

An "enhancer" is a short (50-1500 bp) region of DNA that can be bound with one or more activator proteins (transcription factors) to activate transcription of a gene.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques.

A "variant" of a polypeptide (e.g., an immunoglobulin, or an antibody) comprises an amino acid sequence wherein one or more amino acid residues are inserted into, deleted from and/or substituted into the amino acid sequence relative to another polypeptide sequence. Variants include fusion proteins.

The term "fusion protein," for example with respect to aflibercept, indicates that the protein includes polypeptide components derived from more than one parental protein or polypeptide. Typically, a fusion protein is expressed from a "fusion gene" in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "secreted" protein refers to those proteins capable of being directed to the endoplasmic reticulum (ER), secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments, the aflibercept fusion protein of interest can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes, or, in vitro, is dissolved, or is capable of being dissolved in an aqueous buffer under physiological conditions without forming significant amounts of insoluble aggregates (i.e., forms aggregates less than 10%, and typically less than about 5%, of total protein) when it is suspended without other proteins in an aqueous buffer of interest under physiological conditions, such buffer not containing an ionic detergent or chaotropic agent, such as sodium dodecyl sulfate (SDS), urea, guanidinium hydrochloride, or lithium perchlorate. In contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc., or in an in vitro aqueous buffer under physiological conditions forms significant amounts of insoluble aggregates (i.e., forms aggregates equal to or more than about 10% of total protein) when it is suspended without other proteins (at physiologically compatible temperature) in an aqueous buffer of interest under physiological conditions, such buffer not containing an ionic detergent or chaotropic agent, such as sodium dodecyl sulfate (SDS), urea, guanidinium hydrochloride, or lithium perchlorate.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the immunoglobulin (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

An expression cassette is a typical feature of recombinant expression technology. The expression cassette includes a gene encoding a protein of interest, e.g., a gene encoding an aflibercept fusion protein sequence. A eukaryotic "expression cassette" refers to the part of an expression vector that enables production of protein in a eukaryotic cell, such as a mammalian cell. It includes a promoter, operable in a eukaryotic cell, for mRNA transcription, one or more gene(s) encoding protein(s) of interest and a mRNA termination and processing signal. An expression cassette can usefully include among the coding sequences, a gene useful as a selective marker. In the expression cassette promoter is operably linked 5' to an open reading frame encoding an exogenous protein of interest; and a polyadenylation site is operably linked 3' to the open reading frame. Other suitable control sequences can also be included as long as the expression cassette remains operable. The open reading frame can optionally include a coding sequence for more than one protein of interest.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

Recombinant expression technology typically involves the use of a recombinant expression vector comprising an expression cassette.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1). For expression of multi-subunit proteins of interest, separate expression vectors in suitable numbers and proportions, each containing a coding sequence for each of the different subunit monomers, can be used to transform a host cell. In other embodiments, a single expression vector can be used to express the different subunits of the protein of interest.

Recombinant expression technology typically involves a mammalian host cell comprising the recombinant expression vector.

The term "host cell" means a cell that has been transformed, or is capable of being transformed, with a nucleic acid and thereby expresses a gene or coding sequence of interest. The term includes the progeny of the parent cell, whether or not the progeny is identical in morphology or in genetic make-up to the original parent cell, so long as the gene of interest is present. Any of a large number of available and well-known host cells may be used in the practice of this invention to obtain aflibercept. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, algal or algal-like cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

Examples of useful mammalian host cell lines are Chinese hamster ovary cells, including CHO-K1 cells (e.g., ATCC CCL61), DXB-11, DG-44, and Chinese hamster ovary cells/-DHFR (CHO, Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture (Graham et al, J. Gen Virol. 36: 59 (1977)); baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

"Cell," "cell line," and "cell culture" are often used interchangeably and all such designations herein include cellular progeny. For example, a cell "derived" from a CHO cell is a cellular progeny of a Chinese Hamster Ovary cell, which may be removed from the original primary cell parent by any number of generations, and which can also include a transformant progeny cell. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Host cells are transformed or transfected with the above-described nucleic acids or vectors for production of polypeptides (including antigen binding proteins, such as antibodies) and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides, such as antibodies.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The host cells used to produce the aflibercept fusion polypeptides useful in the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source, such that the physiological conditions of the cell in, or on, the medium promote expression of the protein of interest by the host cell; any other necessary supplements may also be included at appropriate concentrations that would be known to those skilled in the art. The culture conditions, such as temperature (typically, but not necessarily, about 37° C.), pH (typically, but not necessarily, about pH 6.5-7.5), oxygenation, and the like, are those previously used with the host cell selected for expression of the protein of interest, and will be apparent to the ordinarily skilled artisan. The culture medium can include a suitable amount of serum such a fetal bovine serum (FBS), or preferably, the host cells can be adapted for culture in serum-free medium. In some embodiments, the aqueous medium is liquid, such that the host cells are cultured in a cell suspension within the liquid medium. The host cells can be usefully grown in batch culture or in continuous culture systems.

In other embodiments, the mammalian host cells can be cultured on solid or semi-solid aqueous medium, for example, containing agar or agarose, to form a medium or substrate surface to which the cells adhere and form an adhesion layer.

Upon culturing the host cells, the recombinant polypeptide can be produced intracellularly, in the periplasmic space, or directly secreted into the medium. If the polypeptide, such as aflibercept, is produced intracellularly, as a first step, the particulate debris, either host cells or lysed fragments, is removed, for example, by centrifugation or ultrafiltration.

A protein of interest, such as aflibercept, can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., J. Immunol. Meth. 62: 1-13 (1983)). Protein G is recommended for all mouse isotypes and for human γ3 (Guss et al, EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH 3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

"Under physiological conditions" with respect to incubating buffers and immunoglobulins, or other binding assay reagents means incubation under conditions of temperature, pH, and ionic strength, that permit a biochemical reaction, such as a non-covalent binding reaction, to occur. Typically, the temperature is at room or ambient temperature up to about 37° C. and at pH 6.5-7.5.

"Physiologically acceptable salt" of a composition of matter, for example a salt of a protein of interest, e.g., a fusion protein or an immunoglobulin, such as an antibody, or any other protein of interest, or a salt of an amino acid, such as, but not limited to, a lysine, histidine, or proline salt, means any salt, or salts, that are known or later discovered to be pharmaceutically acceptable. Some non-limiting examples of pharmaceutically acceptable salts are: acetate salts; trifluoroacetate salts; hydrohalides, such as hydrochloride (e.g., monohydrochloride or dihydrochloride salts) and hydrobromide salts; sulfate salts; citrate salts; maleate salts; tartrate salts; glycolate salts; gluconate salts; succinate salts; mesylate salts; besylate salts; salts of gallic acid esters (gallic acid is also known as 3,4,5 trihydroxybenzoic acid) such as PentaGalloylGlucose (PGG) and epigallocatechin gallate (EGCG), salts of cholesteryl sulfate, pamoate salts, tannate salts, and oxalate salts.

A "reaction mixture" is an aqueous mixture containing all the reagents and factors necessary, which under physiological conditions of incubation, permit an in vitro biochemical reaction of interest to occur, such as a covalent or non-covalent binding reaction.

A "domain" or "region" (used interchangeably herein) of a polynucleotide is any portion of the entire polynucleotide, up to and including the complete polynucleotide, but typically comprising less than the complete polynucleotide. A domain can, but need not, fold independently (e.g., DNA hairpin folding) of the rest of the polynucleotide chain and/or be correlated with a particular biological, biochemical, or structural function or location, such as a coding region or a regulatory region.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

Quantification of aflibercept fusion protein, is often useful or necessary in tracking protein production or for lot release assays of drug substance or drug product containing aflibercept. An antibody that specifically binds aflibercept, particularly a monoclonal antibody, can therefore be useful for these purposes.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

An "isolated" protein, e.g., an aflibercept fusion protein, is one that has been identified and separated from one or more components of its natural environment or of a culture medium in which it has been secreted by a producing cell. In some embodiments, the isolated protein is substantially free from proteins or polypeptides or other contaminants that are found in its natural or culture medium environment that would interfere with its therapeutic, diagnostic, prophylactic, research or other use. "Contaminant" components of its natural environment or medium are materials that would interfere with diagnostic or therapeutic uses for the protein, e.g., an antibody, and may include enzymes, hormones, and other proteinaceous or nonproteinaceous (e.g., polynucleotides, lipids, carbohydrates) solutes. Typically, an "isolated protein" constitutes at least about 5%, at least about 10%, at least about 25%, or at least about 50% of a given sample. In some embodiments, the protein of interest, e.g., aflibercept fusion protein or an antibody, will be purified (1) to greater than 95% by weight of protein, and most preferably more than 99% by weight, or (2) to homogeneity by SDS-PAGE, or other suitable technique, under reducing or nonreducing conditions, optionally using a stain, e.g., Coomassie blue or silver stain. Isolated naturally occurring antibody includes the antibody in situ within recombinant cells since at least one component of the protein's natural environment will not be present. Typically, however, the isolated protein of interest (e.g., aflibercept or an antibody) will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies that are antigen binding proteins are highly specific binders, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"). An "immunoglobulin" is a protein, but is not necessarily an antigen binding protein.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is an antigen binding protein. The variable domain residues between the hypervariable regions are called the framework residues and generally are somewhat homologous among different antibodies Immunoglobulins can be assigned to different classes depending on the amino acid sequence of the constant domain of their heavy chains. Human light chains are classified as kappa (.kappa.) and lambda (.lamda.) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). An "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the carboxy-terminus of the polypeptide. Heavy chains are classified as mu (μ), delta (δ), gamma (γ), alpha (α), and epsilon (ε), and define the antibody's isotype as IgM, IgD, IgG, IgA, and IgE, respectively. Heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (Fc.gamma.Rs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_{H1}$ and $C_{H2}$ domains of the antibody. The two heavy chain fragments are held together by two or more disulfide bonds and by hydrophobic interactions of the $C_{H3}$ domains.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and JH segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, th Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or "FR" residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10): 1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')$_2$ fragment that has two "Single-chain Fv" or "scFv" antibody fragments comprising the $V_H$ and $V_L$ domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and a portion of one heavy chain that contains the $V_H$ domain and the CH1 domain and also the region between the $C_{H1}$ and $C_{H2}$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference in their entireties.

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Natl. Acad. Sci. USA 85:5879-5883, 1988). An "Fd" fragment consists of the $V_H$ and $C_{H1}$ domains.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "antigen binding protein" (ABP) includes aflibercept, or antibodies or antibody fragments, as defined herein, and recombinant peptides or other compounds that contain sequences derived from CDRs having the desired antigen-binding properties such that they specifically bind a target antigen of interest.

In general, an antigen binding protein, e.g., aflibercept or an antibody or antibody fragment, "specifically binds" to an antigen of interest when it has a significantly higher binding affinity for, and consequently is capable of distinguishing, that antigen, compared to its affinity for other unrelated proteins, under similar binding assay conditions. Typically, an antigen binding protein is said to "specifically bind" its target antigen when the dissociation constant ($K_D$) is $10^{-8}$ M or lower. The antigen binding protein specifically binds antigen with "high affinity" when the $K_D$ is $10^{-9}$ M or lower, and with "very high affinity" when the $K_D$ is $10^{-10}$ M or lower.

"Antigen binding region" or "antigen binding site" means a portion of a protein that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions ("FRs"). A "CDR" is an amino acid sequence that contributes to antigen binding specificity and affinity. "Framework" regions can aid in maintaining the proper conformation of the CDRs to promote binding between the antigen binding region and an antigen. In a traditional antibody, the CDRs are embedded within a framework in the heavy and light chain variable region where they constitute the regions responsible for antigen binding and recognition. A variable region of an immunoglobulin antigen binding protein comprises at least three heavy or light chain CDRs, see, supra (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991, supra; see also Chothia and Lesk, 1987, supra).

The term "antigen" refers to a molecule or a portion of a molecule capable of being bound by a selective binding agent, such as an antigen binding protein (including, e.g., aflibercept, or an antibody or immunologically functional fragment of an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, aflibercept or an antibody). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with proteins of interest, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. By methods known to the skilled artisan, proteins, can be "engineered" or modified for improved target affinity, selectivity, stability, and/or manufacturability before the coding sequence of the "engineered" protein is included in the expression cassette.

The term "derivative" when used in connection with proteins of interest, such as aflibercept or antibodies, refers to proteins that are covalently modified by conjugation to therapeutic or diagnostic agents, labeling (e.g., with radionuclides or various enzymes), covalent polymer attachment such as PEGylation (derivatization with polyethylene glycol) and insertion or substitution by chemical synthesis of non-natural amino acids.

Within the scope of the invention, aflibercept proteins can be therapeutic proteins, or "biologics," for the treatment of disease, including but not limited to human disease or disorder, e.g., a disease or disorder of the eye. "Treatment" or "treating" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. "Treatment" includes any indication(s) of success in the amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination by a physician, e.g., an ophthalmologist, or other health care provider, or self-reporting by a patient.

An "effective amount" of a therapeutic is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with an eye disorder or disease. In some embodiments, the effective amount is a therapeutically effective amount or a prophylactically effective amount. A "therapeutically effective amount" is an amount sufficient to remedy a disease state (e.g., macular edema following Central Retinal Vein Occlusion (CRVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD), transplant rejection or GVHD, inflammation, multiple sclerosis, cancer, cardiovascular disease, diabetes, neuropathy, pain) or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of a pharmaceutical composition that, when administered to a subject, will have the intended prophylactic effect. The full therapeutic or prophylactic effect does not necessarily occur by administration of one dose, and may occur only after administration of a series of doses. Thus, a therapeutically or prophylactically effective amount may be administered in one or more administrations.

Cloning DNA

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the polypeptide of interest, e.g., of the aflibercept fusion polypeptide sequence.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

Sequencing of DNA is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of genes and cDNAs, one of skill will readily be able to determine, depending on the region sequenced. One source of gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the expressed protein; an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Purity of Water and Other Ingredients.

The water and all other ingredients that are used to make the inventive ophthalmic formulations are preferably of a level of purity meeting the applicable legal or pharmacopoeial standards required for such pharmaceutical compositions and medicaments in the jurisdiction of interest, e.g., United States Pharmacopeia (USP), European Pharmacopeia, Japanese Pharmacopeia, or Chinese Pharmacopeia, etc. For example, according to the USP, Water for Injection is used as an excipient in the production of parenteral and other preparations where product endotoxin content must be controlled, and in other pharmaceutical applications, such as cleaning of certain equipment and parenteral product-contact components; and the minimum quality of source or feed water for the generation of Water for Injection is Drinking Water as defined by the U.S. Environmental Protection Agency (EPA), EU, Japan, or WHO.

Before administration to a patient, the inventive formulations should meet the applicable legal or pharmacopoeial standards required for such pharmaceutical compositions and medicaments in the jurisdiction of interest as to sterility, lack of endotoxin or viral contaminants, etc.

Buffer Systems

The ophthalmic formulation of the invention includes a buffer in the range of about 5 to 50 mM concentration. A suitable buffer system for the inventive ophthalmic formulation can be chosen from a phosphate buffer, histidine buffer, acetate buffer, succinate buffer, citrate buffer, glutamate, and lactate, or the buffer can be a combination of two or more of these buffer systems. Some useful embodiments of the invention have a buffer concentration in the range of about 5 mM to about 20 mM, and other embodiments have a buffer concentration of about 5 to about 10 mM. If a histidine buffer is selected, a histidine concentration in the range of about 5-20 mM is preferred.

Non-Ionic Surfactants

The inventive ophthalmic formulation includes a non-ionic surfactant, preferably at a concentration of about 0.001% (w/v) to about 5.0% (w/v). In some embodiments the concentration of the non-ionic surfactant is about 0.001% (w/v) to about 2.0% (w/v), or about 0.001% (w/v) to about 1.0% (w/v), or about 0.001% (w/v) to about 0.10% (w/v), or about 0.001% (w/v) to about 0.01% (w/v). A useful non-ionic surfactant can be a polysorbate (e.g., polysorbate 20 or polysorbate 80), Brij®35 (i.e., polyethylene glycol dodecyl ether), a poloxamer (i.e., Polyethylene-Polypropylene Glycol; Polyoxyethylene-Polyoxypropylene Block Copolymer; Poly(Ethylene oxide-co-Polypropylene oxide)) such as Poloxamer 188 (i.e., Pluronic F68), or Triton™ X-100 (i.e., 4-(1,1,3,3-Tetramethylbutyl)phenyl-polyethylene glycol)). Also encompassed within "non-ionic surfactant" for purposes of practicing the present invention are alkylsaccharides or alkylglycosides (e.g., sold under the trade name ProTek® by Aegis Therapeutics, LLC; see, e.g., Maggio, Stabilizing Alkylglycoside Compositions And Methods Thereof, U.S. Pat. No. 8,133,863 B2).

Tonicifying Agents

The inventive ophthalmic formulation includes a tonicifying agent such that the formulation has a final osmolality of about 300 mOsm/kg (i.e., 300±50 mOsm/kg) and the chloride anion concentration is less than about 10 mM, preferably less than about 5 mM, and more preferably less than about 1 mM. Osmolality is a measure of the number of dissolved particles per unit of water. In a solution, the fewer the number of particles of solute in proportion to the number of units of water (solvent), the less concentrated the solution, hypo-osmotic. If a semi-permeable membrane (one that is permeable only to solvent molecules) is used to separate solutions of different solute concentrations, a phenomenon known as osmosis occurs in which solvent molecules cross the membrane from lower to higher concentration to establish a concentration equilibrium. The pressure driving this movement is called osmotic pressure and is governed by the number of "particles" of solute in solution. Solutions containing the same concentration of particles and thus exerting equal osmotic pressures are called iso-osmotic. For example, the osmotic pressure within a red blood cell (rbc) is equal to the surrounding solution so that it neither shrinks or expands. If a rbc is placed in water it will burst since the water alone is hypo-osmotic. If the rbc is placed in a high salt solution, i.e. greater than 0.9% (w/v) sodium chloride, it will shrink since the solution is hyper-osmotic. In both examples the rbc is damaged. The same will happen with any biological cell, such as those within the eye. If a hypo- or hyper-osmotic solution is placed on the eye it will cause damage, thus necessitating the need for an iso-osmotic solution for drugs used for the eye. In practice, a 0.9% (w/v) solution of sodium chloride is iso-osmotic and has a concentration of 270-300 mOsm/kg. All solutions are compared to this standard and are considered iso-osmotic if they fall within the expanded range of 250-350 mOsm/kg. Excipients used to stabilize proteins are added at concentrations to produce iso-osmotic solutions. For example, disaccharides such as sucrose and trehalose are iso-osmotic at concentrations of 9.25%, monosaccharides such as glucose and mannose are iso-osmotic at concentrations of 5%, and amino acids such as proline are iso-osmotic at concentrations of approximately 3%. Osmolality can be determined either theoretically or experimentally. Theoretical calculations can be determined according to the following equation:

Osmolality=(g compound/100 mL solution)*(Compound's E-value).

A compound's E-value is determined by the equation:

E-value=(MW NaCl/i-value NaCl)*(i-value compound/MW compound).

The i-value is the number of ions from a compound based on a theoretical dissociation of 80%. For a compound that does not dissociate, i.e. sucrose, the i-value is 1. For a compound that dissociates into 2 ions, i.e. NaCl, the i-value is 1.8 and for a compound that dissociates into 3 ions the i-value is 2.6. Since osmolality is a colligative property of the solution, depression of the freezing point due to added solutes or a depression of the vapor pressure are directly related to the total number of solute molecules in a liquid. Each of these principles have been exploited in the art to develop useful instruments that measure osmolality. Either or both types of instruments can be used for biological samples. As an example, a solution with 10 mM sodium phosphate, 40 mM NaCl, 5% (w/v) sucrose and 0.03% (w/v) polysorbate 20 would have a theoretical osmolality of 263 mOsm/kg. In our laboratory, the actual measured value was 270 mOsm/kg, as measured by freezing point depression. This illustrates that the experimental value closely matches the theoretical value, further demonstrating that for purposes of practicing the present invention, either a theoretical or experimental value may be used for determining if a solution is suitable for intravitreal injection based on its osmolality.

A useful tonicifying agent can be a polyol or an amino acid. Examples of useful polyol tonicifying agents include sucrose, trehalose, sorbitol, mannitol, and glycerol. Typically, the concentration of the polyol tonicifying agent is the in the range of 5-10% (w/v), depending on the buffer concentration and other formulation excipients. The concentration of amino acid tonicifying agent is in the range of 2-4% (w/v), depending on buffer concentration and other tonicifying agents used. In the inventive ophthalmic formulation, the amino acid tonicifying agent can be a L-amino acid form and/or a D-amino acid form, if pharmaceutically acceptable. Encompassed also within the meaning of "amino acid tonicifying agent" is a pharmaceutically acceptable amino acid salt form.

Additional Stabilizing Agents

In some embodiments of the inventive ophthalmic formulation in which the tonicifying agent is a polyol, e.g., sucrose, trehalose, sorbitol, mannitol, or glycerol, the formulation also contains an additional amino acid stabilizing agent. The additional amino acid stabilizing agent can be, for example, proline, arginine, methionine, glycine, or lysine. The additional amino acid stabilizing agent can be an L-amino acid or a D-amino acid, or a salt form, as long as the amino acid is pharmaceutically acceptable, and in a pharmaceutically acceptable form, e.g., a pharmaceutically acceptable salt form. (See, e.g., Falconer et al., *Stabilization of a monoclonal antibody during purification and formulation by addition of basic amino acid excipients*, J Chem Technol Biotechnol (2011) 86: 942-948; Platts et al., *Control of Globular Protein Thermal Stability in Aqueous Formulations by the Positively Charged Amino Acid Excipients*, Journal of Pharmaceutical Sciences 105 (2016) 3532-3536; Wang, W., *Instability, stabilization, and formulation of liquid protein pharmaceuticals*, International Journal of Pharmaceutics 185 (1999) 129-188; Yin et al., *Effects of Antioxidants on the Hydrogen Peroxide-Mediated Oxidation of Methionine Residues in Granulocyte Colony-Stimulating Factor and Human Parathyroid Hormone Fragment 13-34*, Pharmaceutical Research (2004) 21(12):2377-2383; Lam et al., *Antioxidants for Prevention of Methionine Oxidation in Recombinant Monoclonal Antibody HER2*, Journal of Pharmaceutical Sciences 86(11): 1250-1255 (1997); Levine et al., *Methionine Residues as Endogenous Antioxidants in Proteins*, Proc. Natl. Acad. Sci. (USA) 93(26):15036-15040 (1996); Maeder et al., *Local tolerance and stability up to 24 months of a new 20% proline-stabilized polyclonal immunoglobulin for subcutaneous administration*, Biologicals 39:43-49 (2011); Cramer et al., *Stability over 36 months of a new liquid 10% polyclonal immunoglobulin product (IgPro10, Privigen©) stabilized with L-proline*, Vox Sanguinis (2009) 96, 219-225; Bolli et al., *L-Proline reduces IgG dimer content and enhances the stability of intravenous immunoglobulin (IVIG) solutions*, Biologicals 38 (2010) 150-157; Truong, *Combination of D-Amino Acids and Lipoteichoic Acid*, EP2545909 A1; Stroppolo et al., *Pharmaceutical compositions containing the salts of S(+)-2-(4-isobutylphenyl)propionic acid with basic aminoacids*, U.S. Pat. No. 5,510,385). The concentration of the additional amino acid stabilizing agent in combination with the polyol is usefully about 0.01-3% (w/v), depending on the concentration of polyol in combination with the amino acid. However, if methionine is selected in combination with a polyol tonicifying agent, methionine can be used as a scavenger of reactive oxygen species at a low concentration, i.e., 10 mM or less.

EXEMPLARY FORMULATIONS OF THE INVENTIONS

Exemplary ophthalmic formulations of the present invention include those in which the buffer is a phosphate buffer. In one such embodiment (a) the aflibercept concentration is 20-80 mg/mL; (b) the phosphate buffer concentration is about 10 mM; (c) the non-ionic surfactant is polysorbate 20 at a concentration of about 0.03% (w/v); (d) the tonicifying agent is:
(i) sucrose or trehalose at a concentration of about 9% (w/v), or
(ii) proline at a concentration of about 3% (w/v); (e) the concentration of chloride anion is less than about 1 mM; and the pH of the formulation is about pH 6.0 to about pH 6.5. In some preferred embodiments of this formulation, the tonicifying agent is sucrose or trehalose at a concentration of about 9% (w/v), with the aflibercept concentration at about 30 mg/mL to about 50 mg/mL; for example, a concentration of about 40 mg/mL. In other preferred embodiments the tonicifying agent is proline at a concentration of about 3% (w/v), with the aflibercept concentration at about 30 mg/mL to about 50 mg/mL; for example, a concentration of about 40 mg/mL.

Exemplary ophthalmic formulations of the present invention also include those in which the buffer is a histidine buffer at a concentration of 5-20 mM. In one such embodiment (a) the aflibercept concentration is 20-80 mg/mL; (b) the histidine buffer concentration is about 10 mM; (c) the non-ionic surfactant is polysorbate 20 at a concentration of about 0.03% (w/v); (d) the tonicifying agent is:
(i) sucrose or trehalose at a concentration of about 9% (w/v), or
(ii) proline at a concentration of about 3% (w/v); (e) the concentration of chloride anion is less than about 10 mM, or more preferably, less than about 5 mM; and the pH of the formulation is about pH 5.5 to about pH 6.5, or in some embodiments about pH 6.0 to about pH 6.5. In some preferred embodiments of this formulation, the tonicifying agent is sucrose or trehalose at a concentration of about 9% (w/v), with the aflibercept concentration at about 30 mg/mL to about 50 mg/mL; for example, a concentration of about 40 mg/mL. In other preferred embodiments the tonicifying agent is proline at a concentration of about 3% (w/v), with the aflibercept concentration at about 30 mg/mL to about 50 mg/mL; for example, a concentration of about 40 mg/mL.

Still other exemplary ophthalmic formulations of the present invention include those in which the buffer is an acetate buffer. In one such embodiment (a) the aflibercept concentration is 20-80 mg/mL; (b) the acetate buffer is about 10 mM; (c) the non-ionic surfactant is polysorbate 20, or polysorbate 80, or a poloxamer, e.g., Poloxamer 188, at a concentration of about 0.01% (w/v), about 0.03% (w/v), about 0.1 (w/v), or about 1% (w/v); (d) the tonicifying agent is:
(i) sucrose or trehalose at a concentration of about 9% (w/v), or
(ii) proline at a concentration of about 3% (w/v); (e) the concentration of chloride anion is less than about 1 mM; and the pH of the formulation is about pH 5.0 to about pH 5.5. In some preferred embodiments of this formulation, the tonicifying agent is sucrose or trehalose at a concentration of about 9% (w/v), with the aflibercept concentration at about 30 mg/mL to about 50 mg/mL; for example, a concentration of about 40 mg/mL. In other preferred embodiments the tonicifying agent is proline at a concentration of about 3% (w/v), with the aflibercept concentration at about 30 mg/mL to about 50 mg/mL; for example, a concentration of about 40 mg/mL.

By way of further illustration, the following numbered embodiments are encompassed by the present invention:

Embodiment 1: An ophthalmic formulation, comprising:
(a) aflibercept in a concentration of 5-100 mg/mL;
(b) a buffer at 5-50 mM concentration;
(c) a non-ionic surfactant;
(d) a tonicifying agent selected from the group consisting of a polyol and an amino acid, wherein the formulation has a final osmolality of about 300 mOsm/kg, and
(e) wherein the concentration of chloride anion is less than about 10 mM;
and
wherein the pH of the formulation is about pH 5.0 to about pH 6.5.

Embodiment 2: The ophthalmic formulation of Embodiment 1, wherein the concentration of chloride anion is less than about 5 mM.

Embodiment 3: The ophthalmic formulation of Embodiments 1-2, wherein the concentration of chloride anion is less than about 1 mM.

Embodiment 4: The ophthalmic formulation of Embodiments 1-3, wherein the buffer is a phosphate buffer.

Embodiment 5: The ophthalmic formulation of Embodiments 1-3, wherein the buffer is a histidine buffer at a concentration of 5-20 mM.

Embodiment 6: The ophthalmic formulation of Embodiments 1-3, wherein the buffer is an acetate buffer.

Embodiment 7: The ophthalmic formulation of Embodiments 1-3, wherein the buffer is selected from phosphate, histidine, acetate, succinate, citrate, glutamate, and lactate, or is a combination of two or more of these.

Embodiment 8: The ophthalmic formulation of Embodiments 1-7, wherein the buffer concentration is 5-20 mM.

Embodiment 9: The ophthalmic formulation of Embodiments 1-8, wherein the non-ionic surfactant is selected from the group consisting of a polysorbate (e.g., polysorbate 20 or polysorbate 80), a polyethylene glycol dodecyl ether (i.e., Brij® 35), a poloxamer (e.g., Poloxamer 188), 4-(1,1,3,3-Tetramethylbutyl)phenyl-polyethylene glycol (i.e., Triton™ X-100), an alkylsaccharide and an alkylglycoside.

Embodiment 10: The ophthalmic formulation of Embodiments 1-9, wherein the non-ionic surfactant is Poloxamer 188.

Embodiment 11: The ophthalmic formulation of Embodiments 1-10, wherein the tonicifying agent is a polyol selected from sucrose, trehalose, sorbitol, mannitol, and glycerol.

Embodiment 12: The ophthalmic formulation of Embodiments 1-11, wherein the tonicifying agent is sucrose.

Embodiment 13: The ophthalmic formulation of Embodiments 1-11, wherein the tonicifying agent is trehalose.

Embodiment 14: The ophthalmic formulation of Embodiment 11, further comprising an additional amino acid stabilizing agent.

Embodiment 15: The ophthalmic formulation of Embodiment 14, wherein the additional amino acid stabilizing agent is selected from the group consisting of proline, arginine, methionine, glycine, and lysine.

Embodiment 16: The ophthalmic formulation of Embodiments 1-15, wherein the tonicifying agent is an amino acid selected from proline, arginine, aspartate, glutamate, glycine, histidine, isoleucine, and lysine.

Embodiment 17: The ophthalmic formulation of Embodiments 1-16, wherein the tonicifying agent is proline.

Embodiment 18: The ophthalmic formulation of Embodiment 4, wherein:
(a) the aflibercept concentration is 20-80 mg/mL;
(b) the phosphate buffer concentration is about 10 mM,
(c) the non-ionic surfactant is a polysorbate or a poloxamer,
(d) the tonicifying agent is (i) sucrose or trehalose at a concentration of about 9% (w/v) or (ii) proline at a concentration of about 3% (w/v);
(e) the concentration of chloride anion is less than about 1 mM;
and the pH of the ophthalmic formulation is about pH 6.0 to about pH 6.5.

Embodiment 19: The ophthalmic formulation of Embodiment 18, wherein the tonicifying agent is sucrose or trehalose at a concentration of about 9% (w/v).

Embodiment 20: The ophthalmic formulation of Embodiment 18, wherein the tonicifying agent is proline at a concentration of about 3% (w/v).

Embodiment 21: The ophthalmic formulation of Embodiment 5, wherein:
(a) the aflibercept concentration is 20-80 mg/mL;
(b) the histidine buffer is about 10 mM;
(c) the non-ionic surfactant is a polysorbate or a poloxamer;
(d) the tonicifying agent is (i) trehalose at a concentration of about 9% (w/v) or (ii) proline at a concentration of about 3% (w/v);
and the pH of the ophthalmic formulation is about pH 5.5 to about pH 6.5.

Embodiment 22: The ophthalmic formulation of Embodiment 21, wherein the tonicifying agent is trehalose at a concentration of about 9% (w/v).

Embodiment 23: The ophthalmic formulation of Embodiment 21, wherein the tonicifying agent is proline at a concentration of about 3% (w/v).

Embodiment 24: The ophthalmic formulation of Embodiment 6, wherein:
(a) the aflibercept concentration is 20-80 mg/mL;
(b) the acetate buffer is about 10 mM;
(c) the non-ionic surfactant is a polysorbate or a poloxamer;
(d) the tonicifying agent is (i) sucrose or trehalose at a concentration of about 9% (w/v) or (ii) proline at a concentration of about 3% (w/v);
(e) the concentration of chloride anion is less than about 1 mM;
and the pH of the ophthalmic formulation is about pH 5.0 to about pH 5.5.

Embodiment 25: Use of any of the formulations of Embodiments 1-24 for the treatment of an eye disorder or disease.

Embodiment 26: The use of Embodiment 25, wherein the eye disorder or disease is selected from macular edema following Retinal Vein Occlusion (RVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD).

Embodiment 27: The use of Embodiments 25-26, wherein the ophthalmic formulation is administered to a patient with the eye disorder or disease by intravitreal injection.

The following working examples are illustrative and not to be construed in any way as limiting the scope of the invention.

EXAMPLES

Example 1. Stability Studies

Materials. The VEGF-specific aflibercept fusion protein antagonist was produced using industry standard recombinant expression technology and purification processes. The purified drug substance was buffer exchanged against the specified formulation buffers using a bench scale tangential flow filtration system by Millipore Corporation. Protein concentrations were adjusted to the final target concentration by diluting with formulation buffer. The water used in making all formulations was purified by a Milli-Q® (Millipore Corporation) water purification system, which includes an ion exchange cartridge. The purity of the water was monitored by measuring the conductivity, with a value greater than 18.2 MΩ cm-1 (@ 25 Å° C.) being acceptable. All excipients, buffers and other ingredients used for the preparation of formulation buffers were USP grade or equivalent.

Methods.

Titrations: Acid and base conjugates, prepared at equal molarity, were blended together at the appropriate molar ratios to achieve the desired formulation pH for the histidine and phosphate buffer systems. The acetate formulations were prepared using a glacial acetic acid addition to Milli-Q-purified water followed by a sodium hydroxide titration to reach the desired final pH.

Appearance: A qualitative visual appearance test was performed to assess the drug product for protein particles or environment contaminants. An aliquot (1.1 mL) of sample was placed into a pre-sterilized Type 1 glass vial and capped with a 13 mm closure. Under ambient light conditions, the sample was gently swirled and visually inspected for 5 seconds to detect visible particles. For all samples tested, the number and description of any detected particles were recorded.

Color. A qualitative visual color assessment was performed to monitor drug product color during product stability. Commercially available EP 2.2.2 brown-yellow color standards (BY1-BY7) from Ricca Chemicals were aliquoted into pre-sterilized Type 1 glass vials. An aliquot (1.1 mL) of drug product was placed into a vial and compared against an equal volume of each brown-yellow color standard to determine the level of coloration. All samples were inspected in front of a white background and the level of coloration was recorded for each sample.

Reduced Volume Light Obscuration Sub-Visible Particle Analysis. A HIAC counter equipped with an HRLD-150 sensor (Beckman Corporation) was used to measure subvisible particles by light obscuration. The sensor was calibrated using polystyrene beads ranging from 1-100 μm. Prior to analysis, MilliQ water was flushed through the system until a clean baseline was achieved and a standard solution of 15

µm polystyrene beads was used to confirm system suitability. Replicate samples were pooled to a final volume of 1.1 mL in a glass vial and vacuum degassed for 2 hours at 75 Torr. For each sample, the instrument was set to draw five aliquots of 0.2 mL and measure particles greater than 10 µm and 25 µm. The average of the last three measurement were reported.

Size Exclusion Chromatography. Size exclusion high performance liquid chromatography (SE-HPLC) analysis was performed using a Waters XBridge Protein BEH SEC 200A column. Separation was achieved under native conditions using a phosphate, sodium chloride running buffer. Peak elution was detected by UV absorbance, and the integrated purity results were reported as relative peak area percentages of the high molecular weight (HMW) component, main component (monomer), and low molecular weight (LMW) component, relative to total corrected area.

CZE Chloride Ions Analysis. Chloride ion analysis was performed using a Microsolv Technologies CElixirOA pH 5.4 kit run on the Beckman PA. 800 capillary electrophoresis instrument. Samples and standards were prepared according to the manufacturer's instructions. Injection was by pressure at 1 psi for 10 seconds onto a 50.2 cm effective length bare fused capillary. Samples were monitored by a photo diode array detector (PDA). Analysis of a standard curve was used to quantify the concentration of chloride anions in each sample.

Reduced Capillary Electrophoresis—Sodium Dodecyl Sulfate (rCE SDS). Protein samples were denatured by heating at 70° C. for 10 minutes in SDS and reduced with β-mercapto-ethanol. Samples were electrokinetically injected into a 30.2 cm bare fused silica capillary filled with SDS gel buffer. An electrical voltage of −15 kV was applied across the capillary, which separates species by their difference in size. Proteins were detected using a photodiode array detector. The purity was evaluated by determining the percent peak area of each component.

Non-Reduced Capillary Electrophoresis—Sodium Dodecyl Sulfate (nrCE SDS). Samples were denatured by heating at 60° C. for 5 minutes in the presence of SDS and N-ethylmaleimide (NEM) at low pH. The resulting negatively charged SDS-protein complex was electrokinetically injected into a 30.2 cm bare-fused silica capillary filled with SDS gel buffer. An electrical voltage of −15 kV was applied across the capillary, which separates species by their difference in size. Protein species were detected by a photodiode array (PDA) detector as they passed through the detection window. Purity was evaluated by determining the percent peak area of each component.

Capillary Isoelectric Focusing. Capillary Isoelectric focusing (cIEF) was employed to separate proteins based on differences in isoelectric point (pI). The neutral coated capillary was filled with an ampholytic solution and an electric voltage was applied which focuses the ampholytic species into a pH gradient. The protein species were focused into the portion of the pH gradient where the pH is equal to their isoelectric point. Proteins were chemically mobilized and detected by UV absorbance (280 nm) as they passed through a detection window. Purity was evaluated by determining the percent peak area of each component.

Potency Evaluation. Potency of aflibercept was assessed in a cell-based VEGF-A165 dependent proliferation assay. Human umbilical vein endothelial cells were plated in 96-well plates in the absence of growth factors with varying concentrations of drug product and 100 ng/mL of VEGF-A165. Assay plates were incubated for approximately 3 days at 37° C., 5% $CO_2$ before the addition of a fluorescent viability reagent. Dose response curves were generated by graphing drug product concentration versus fluorescence and then fitting with a 4-parameter fit equation. Relative potency was measured by evaluating a shift along the x-axis between the test sample and reference standard.

Osmolality Measurements. The osmolality of the samples was measured using an Advanced Instruments, Inc. freezing point osmometer. Prior to sample analysis, the instrument calibration was checked using a 290 mOsm/kg Clinitrol™ 290 Reference Solution (Fisher Scientific). A 20-µL aliquot subsample from a sample was transferred to a sample tube and placed into the instrument for freezing point analysis. Each sample was analyzed in triplicate and the reported results were an average of these values.

Example 2. Stability Studies

Stability analysis of aflibercept was conducted to understand the importance of chloride ion, pH, buffer, and stabilizer type to the stability of the molecule. The composition of each aflibercept (40 mg/mL) formulation and the abbreviation (i.e., formulation number) used throughout the results of this Example 2 and FIGS. 1-10 herein are outlined in Table 1. Amino acids used were in L-isomeric configuration.

TABLE 1

Formulations studied. Aflibercept concentration was 40 mg/mL.

| Formulation Number | Formulation |
|---|---|
| 1 | 10 mM sodium phosphate, 40 mM sodium chloride, 5% (w/v) sucrose, 0.03% (w/v) polysorbate 20, pH 6.2 |
| 2 | 10 mM sodium phosphate, 9% (w/v) sucrose, 0.03% (w/v) polysorbate 20, pH 6.2 |
| 3 | 10 mM sodium phosphate, 40 mM sodium chloride, 2% (w/v) proline, 0.03% (w/v) polysorbate 20, pH 6.2 |
| 4 | 10 mM sodium phosphate, 3% (w/v) proline, 0.03% (w/v) polysorbate 20, pH 6.2 |
| 5 | 10 mM sodium phosphate, 9% (w/v) Trehalose, 0.03% (w/v) polysorbate 20, pH 6.2 |
| 6 | 10 mM histidine, 3% (w/v) proline, 0.03% (w/v) polysorbate 20, pH 6.2 |
| 7 | 10 mM histidine, 9% (w/v) sucrose, 0.03% (w/v) polysorbate 20, pH 6.2 |
| 8 | 10 mM acetate, 9% (w/v) sucrose, 0.03% (w/v) polysorbate 20, pH 5.2 |

Chloride Ion Detection. Chloride ions levels were measured by capillary zone electrophoresis. Formulation buffers and the formulated drug products were tested to determine the level of chloride ions present in each sample. Drug product samples formulated with sodium chloride or those formulated with histidine are expected to have chloride ions present in the buffer and drug product samples. As shown in Table 2, the formulation buffers with added sodium chloride had the expected level of chloride ions, while histidine formulations without added sodium chloride showed low levels of chloride ions, a result due to the histidine-mono hydrochloride used during the buffer preparation. All formulated drug product samples demonstrated slightly higher levels of chloride ions than the corresponding buffer sample. This result is likely due to residual chloride from the product purification.

TABLE 2

The capillary zone electrophoresis chloride ion results from formulation buffers versus the formulated drug product aflibercept samples. Residual chloride ions from the purification process resulted in slightly elevated chloride ion levels in the drug product samples versus the formulation buffer alone.

| Formulation | Formulation Buffer Cl⁻ Ion Concn (mM) | Formulated Drug Product Cl⁻ Ion Concn (mM) |
| --- | --- | --- |
| 1 | 41.8 | 42.6 |
| 2 | 0.0 | 0.1 |
| 3 | 38.9 | 45.9 |
| 4 | 0.0 | 1.4 |
| 5 | 0.0 | 0.1 |
| 6 | 2.4 | 4.7 |
| 7 | 2.8 | 4.6 |
| 8 | 0.0 | 0.6 |

Osmolality. The osmolality of the drug product solutions was measured to ensure that co-concentration or exclusion of formulation components during the drug product preparation process did not result in unacceptable osmolality levels for intravitreal injection. The osmolality results for the eight drug product formulations evaluated in this study showed osmolality levels within the acceptable 250-350 mOsm/kg range. A summary of these results are shown in Table 3.

TABLE 3

The osmolality of the eight aflibercept formulated drug product samples were measured by a freezing point osmometer, which indicated all samples were within the acceptable range.

| Formulation Number | Osmolality (mOsm/kg) |
| --- | --- |
| 1 | 258 |
| 2 | 326 |
| 3 | 277 |
| 4 | 302 |
| 5 | 320 |
| 6 | 297 |
| 7 | 330 |
| 8 | 332 |

Visual Assessment: Visible Particulates and Color Inspection. The visual assessment of the drug product sample was conducted to determine the presence or absence of environmental or product related particles and to evaluate the product color over the duration of the stability study. Stability samples stored at 4° C. for 7 weeks, and 30° C. for 4 weeks, were inspected for visual particles and all samples passed this assessment.

The color inspection of aflibercept drug product stability samples was conducted by comparing the formulated protein to commercially available brown-yellow pharmacopeia color standards (EP 2.2.2). The results from this assessment determined that regardless of formulation and temperature, the drug product color did not change during storage.

Figure 2:
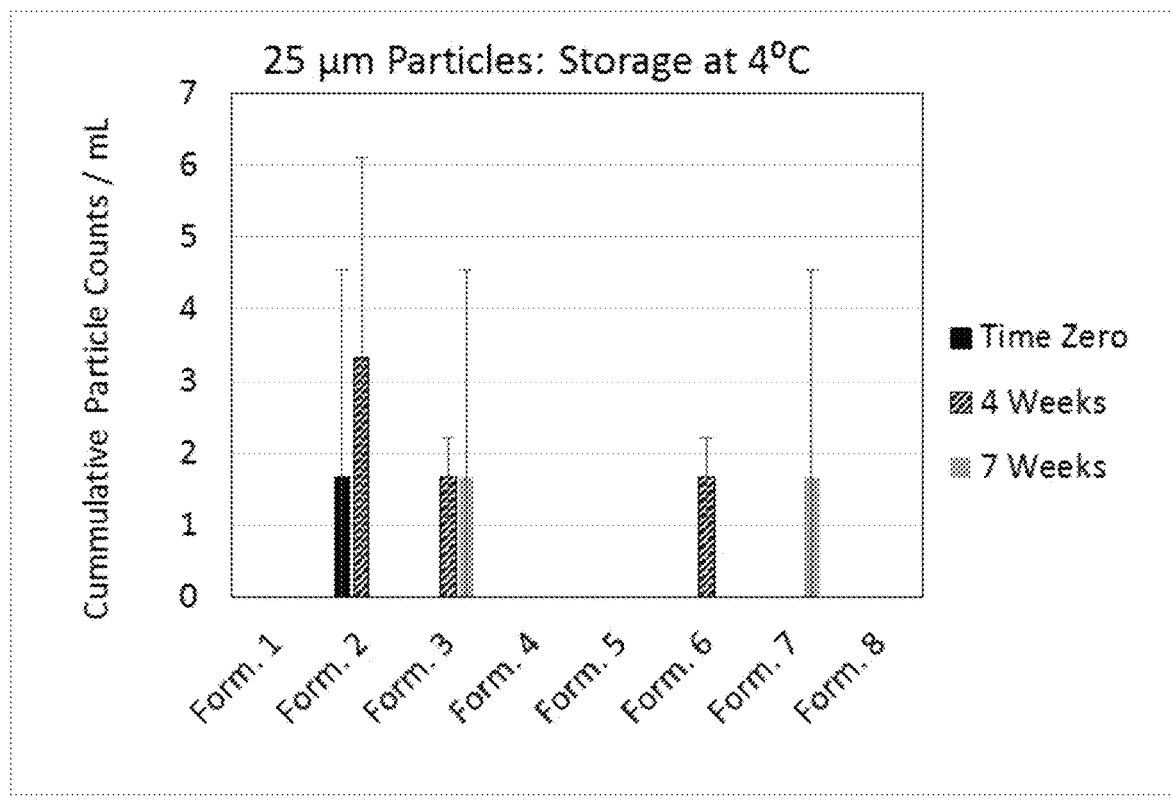
FIG. 2 shows results from subvisible particle analysis, conducted by small volume HIAC analysis. The 25-μm results indicated that all samples had low or undetectable levels of particles. The error bars, representing the standard deviation of three replicate measurements, are larger than the number of particles observed.
Figure 3:
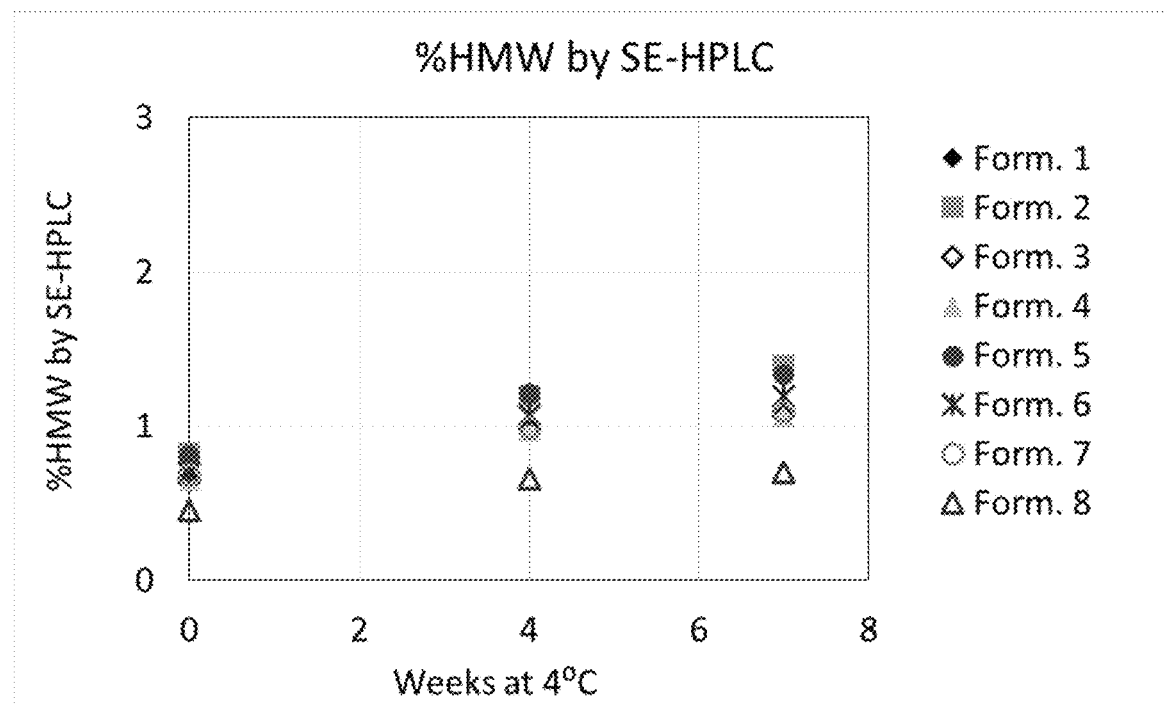
FIG. 3 shows results from size exclusion high performance liquid chromatography of samples stored at 4° C. Apart from Formulation 8, all formulations showed similar rates of HMW formation.
Figure 4:
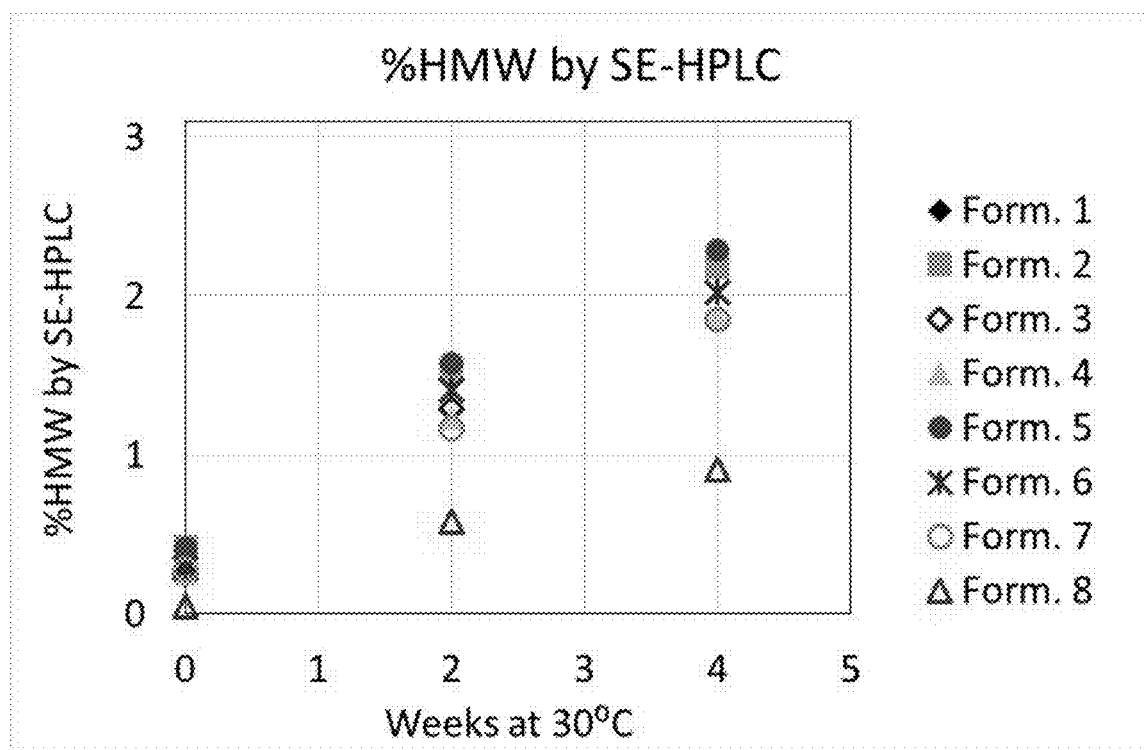
FIG. 4 shows results from size exclusion high performance liquid chromatography of samples stored at 30° C. Apart from Formulation 8, all formulations showed similar rates of HMW formation.
Figure 5:
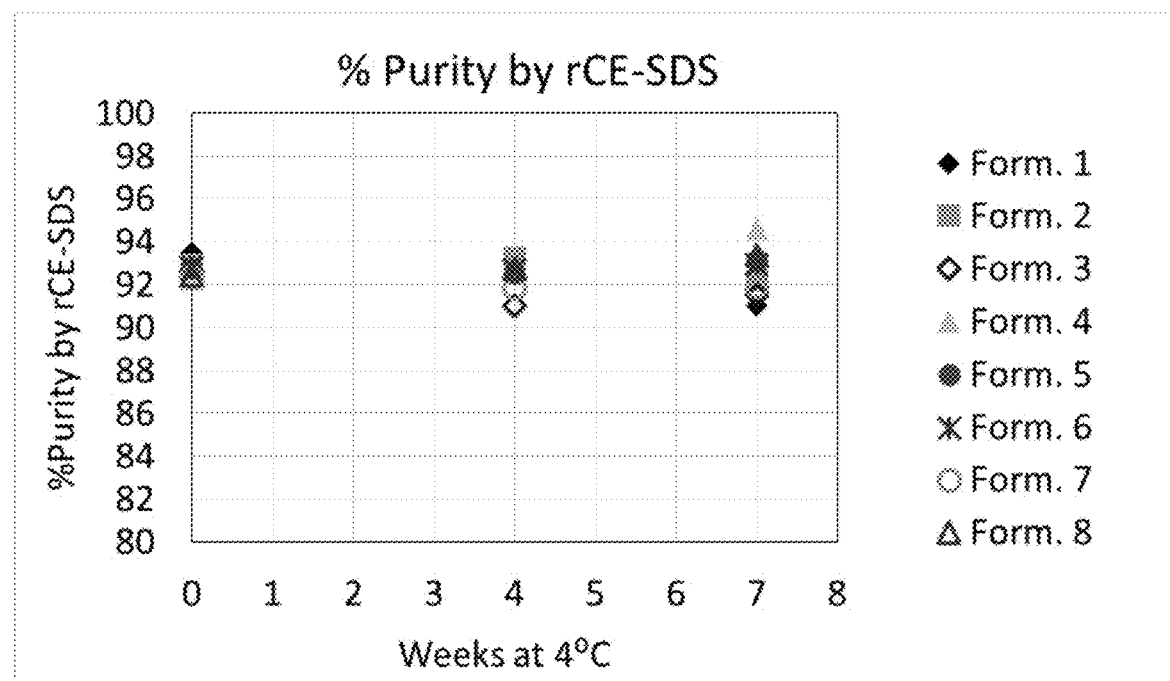
FIG. 5 shows results of the reduced CE-SDS analysis for the 4° C. storage condition. All formulations exhibited similar levels of percent purity during the 7 weeks of testing.

Subvisible Particle Testing: HIAC. Subvisible particle analysis was conducted on the 4° C. stability samples. The 10-μm and 25-μm particle size results are shown in FIG. 1 and FIG. 2, respectively. The error bars in FIG. 1 and FIG. 2 represent the standard deviation calculated from three readings. The measured subvisible particle levels were well below those mandated by USP monograph <789> (*Particulate Matter In Ophthalmic Solutions*). Ten (10)-μm particles were observed for all formulations stored at 4° C., apart from Formulation 7, a condition that had increasing levels of subvisible particles over time. The 25-μm particle levels, shown in FIG. 2 were undetectable or at very low levels when stored at 4° C. It should be noted that the error bars for the 25-μm results are larger than the number of particles reported and therefore no trends can be concluded from these early time point data. SE-HPLC. Size exclusion high performance liquid chromatography (SE-HPLC) analysis was used to evaluate the level of high molecular weight species (HMW) in the stability samples throughout the duration of the study. SE-HPLC was performed at all time points for all temperature conditions. Results from the 4° C. and 30° C. temperature storage conditions are shown in FIG. 3 and FIG. 4, respectively. After 7 weeks of storage at 4° C. Formulations 1-7 had HMW levels that were indistinguishable from each other, which are at an equivalent pH, but have differences in buffer type, tonicity modifier and presence of sodium chloride. Surprisingly, Formulation 8, which had a significantly lower pH than the other formulations, also had dramatically reduced levels of aggregates as compared to the other formulations. The trends observed at 4° C. were comparable to those detected after 4 weeks of storage at 30° C.

The SE-HPLC-measured HMW data imply that sodium chloride is not necessary to stabilize aflibercept during long term storage, for any of the studied formulations, which is surprisingly contrary to the teaching of Dix et al. (See, U.S. Pat. No. 8,921,316, Column 6, lines 62-65; stating that "although either NaCl or sucrose can be used as a stabilizer, a combination of NaCl and sucrose has been established to stabilize the fusion protein more effectively than either individual stabilizer alone," which is contrary to the empirical results we report herein.) Histidine and acetate buffer systems are viable alternatives to phosphate depending on the pH desired. Significantly reduced levels of aggregate could be obtained using a buffer in the pH range around 5. In addition to sucrose, the tonicifying agents proline and trehalose can be used to reach the appropriate osmolality (~300 mOsm/kg) while maintaining or enhancing the aflibercept molecule stability.

Figure 6:
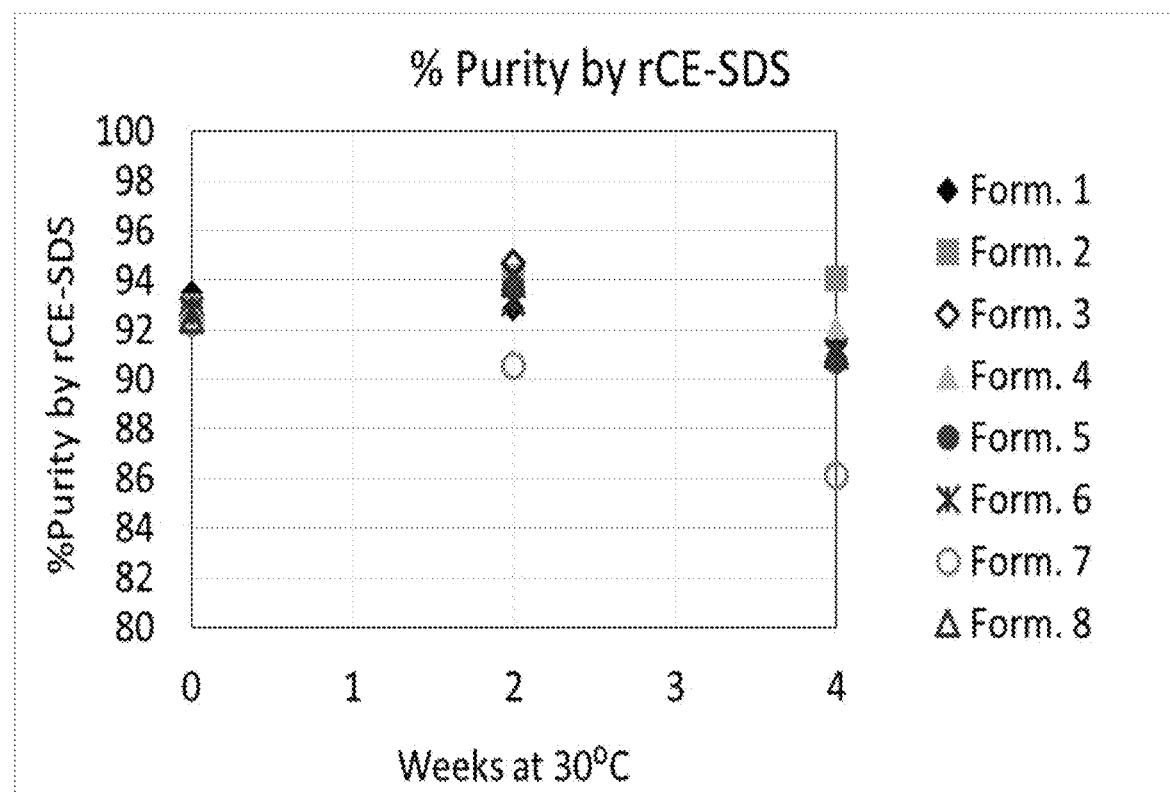
FIG. 6 shows results of the reduced CE-SDS analysis for the 30° C. storage condition. All formulations, except for Formulation 7, exhibited similar levels of percent purity during 30° C. storage. Formulation 7 exhibited a consistent decrease in percent purity over time.
Figure 7:
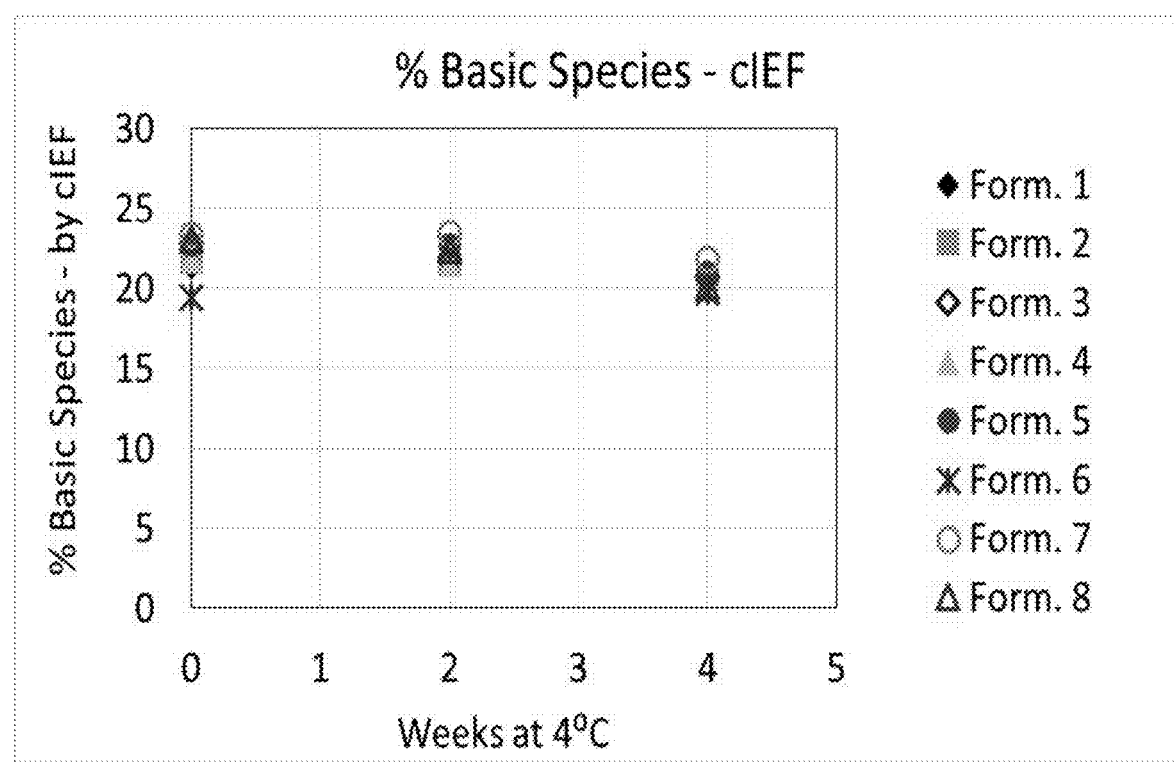
FIG. 7 shows results of the cIEF analysis, used to assess the aflibercept charge distribution during 4° C. storage. All formulations exhibited similar levels of percent basic species over time.
Figure 8:
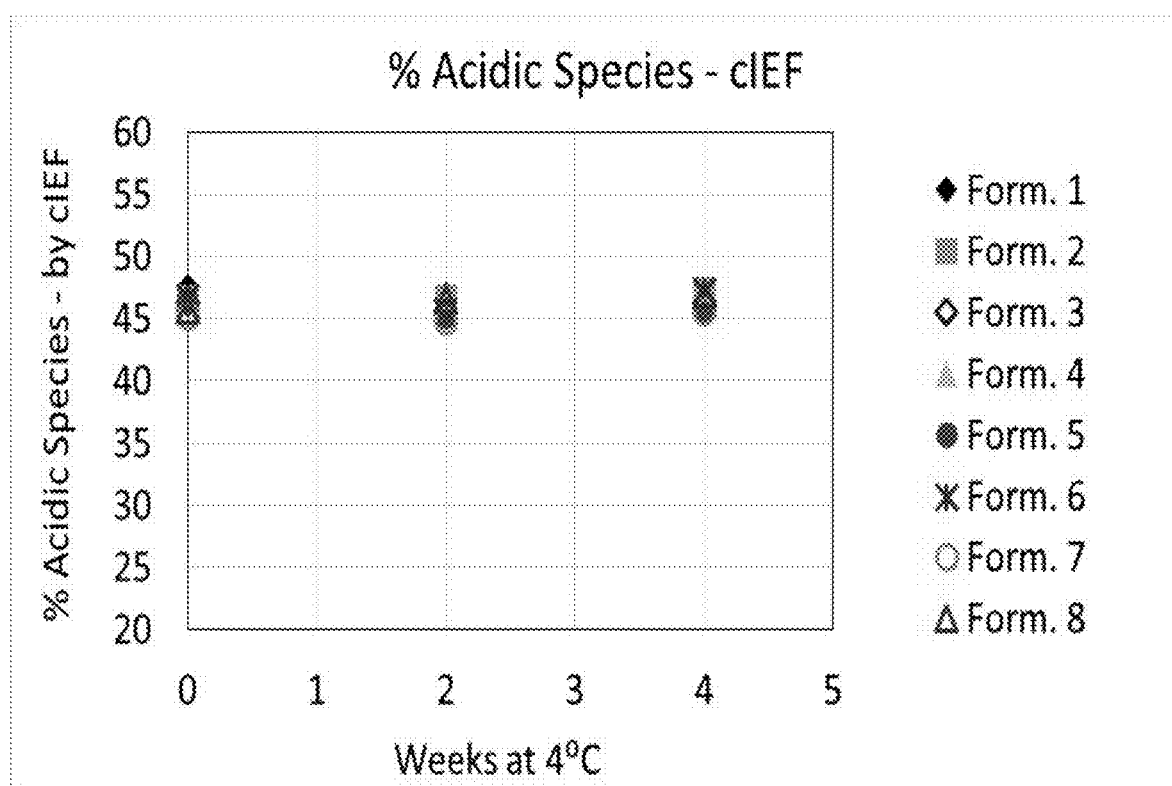
FIG. 8 shows results of cIEF analysis, used to assess the aflibercept charge distribution during 4° C. storage. All formulations exhibited similar levels of percent acidic species over time.
Figure 9:
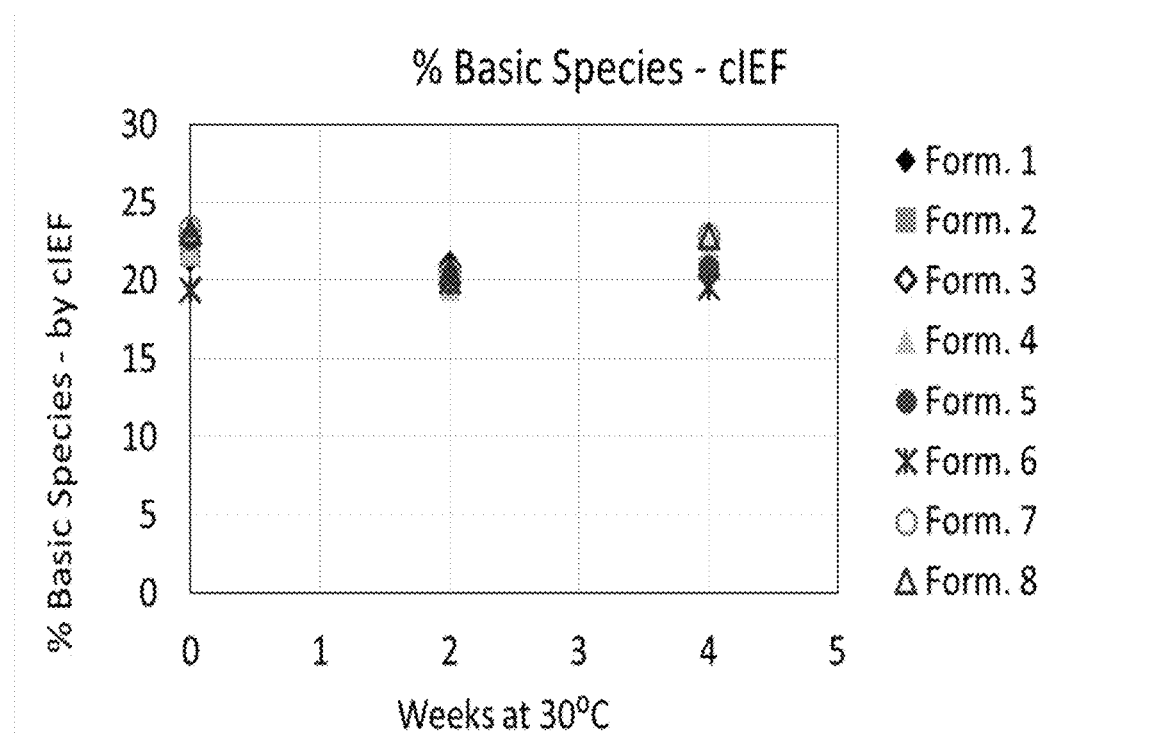
FIG. 9 shows results of cIEF analysis, used to assess the aflibercept charge distribution during 30° C. storage. All formulations exhibited similar levels of percent basic species over time.
Figure 10:
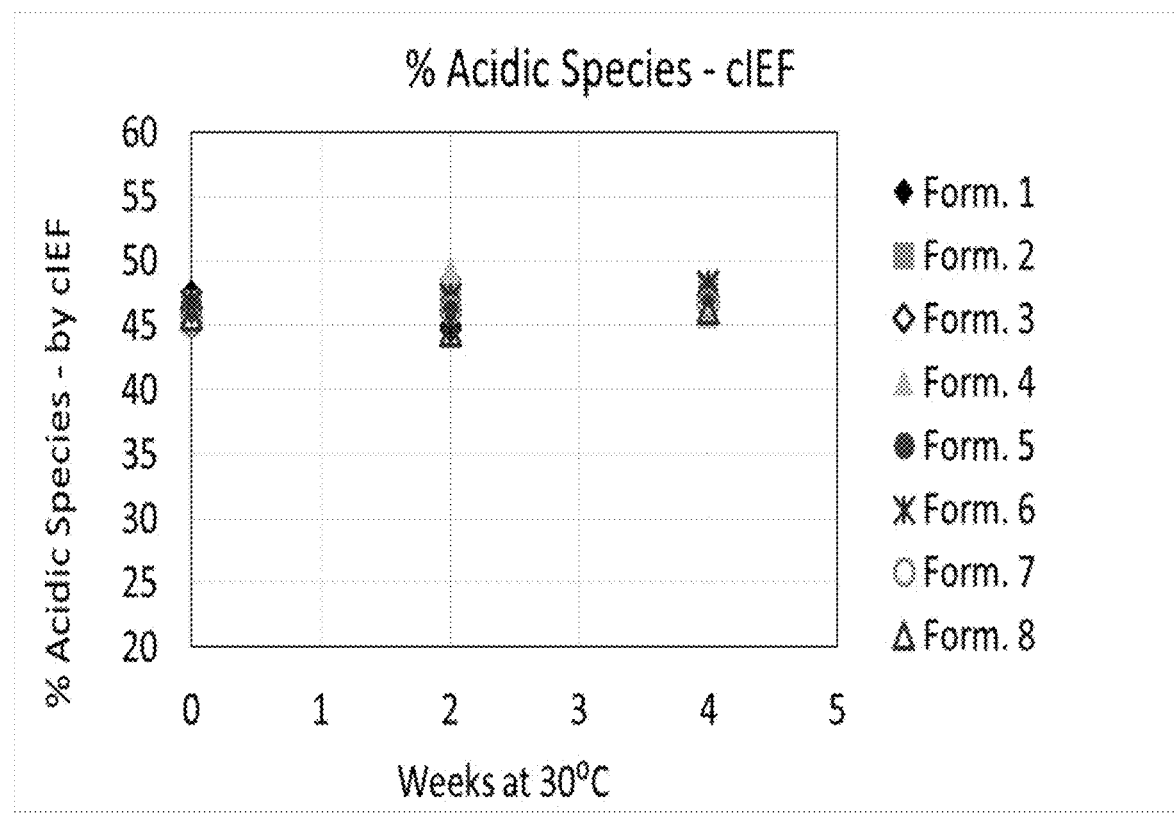
FIG. 10 shows results of cIEF analysis, used to assess the aflibercept charge distribution during 30° C. storage. All formulations exhibited similar levels of percent acidic species over time.

Reduced Capillary Electrophoresis Sodium Dodecyl Sulfate (rCE-SDS). The rCE-SDS method was used to monitor product degradation over time, such as cleavage of the amino acid backbone, with results being reported as percent purity, i.e. the total percent of heavy chain and light chain. The 4° C. results are summarized in FIG. 5, and the 30° C. data are shown in FIG. 6. Regardless of storage temperature, all formulations studied, apart from Formulation 7, have similar levels of purity throughout the tested time points. Numerical differences observed between formulations are within the assay variability. Formulation 7 showed an increase in product degradation at the 30° C. elevated temperature condition, resulting in a decreased percent purity over time.

Capillary Isoelectric Focusing (cIEF). Capillary Isoelectric Focusing (cIEF) was used to monitor changes in the distribution of charge variants over time. To assess the different formulations, the percent basic species levels and percent acidic species levels were plotted against time. An increase or decreases in these species would indicate a change in protein charge, likely resulting from a chemical modification of the peptide backbone. As shown in FIG. 7, FIG. 8, FIG. 9, and FIG. 10, there were no observed changes in the distribution of the charge variants over time. These data indicate no detectable chemical modifications occurred that affected the aflibercept protein's charge.

Example 3. Stability Studies

Further tests of aflibercept stability in various embodiments of the inventive formulation were carried out. Table 4 contains a list of aflibercept (40 mg/mL) formulations tested and their abbreviations. Amino acids used were in L-isomeric configuration.

TABLE 4

Formulations of aflibercept (40 mg/mL) tested and their osmolality and associated abbreviations used in Tables 5-15 herein.

| Abbreviation | Formulation | Osmolality (mOsm/kg ± SD; n = 3) |
|---|---|---|
| P62NaSuT | 10 mM sodium phosphate, 40 mM sodium chloride, 5% (w/v) sucrose, 0.03% (w/v) polysorbate 20, pH 6.2 | 258.7 ± 4.0 |
| A52ProP1-1 | 10 mM acetate, 3% (w/v) proline, 1% (w/v) poloxamer 188, pH 5.2 | 297.7 ± 2.1 |
| A52ProP1-0.1 | 10 mM acetate, 3% (w/v) proline, 0.1% (w/v) poloxamer 188, pH 5.2 | 300.7 ± 2.3 |
| A52ProP1-0.01 | 10 mM acetate, 3% (w/v) proline, 0.01% (w/v) poloxamer 188, pH 5.2 | 304.7 ± 2.5 |
| A52ProT | 10 mM acetate, 3% (w/v) proline, 0.03% (w/v) polysorbate 80, pH 5.2 | 299.0 ± 0.0 |
| P62ProP1-0.1 | 10 mM sodium phosphate, 3% (w/v) proline, 0.1% (w/v) poloxamer 188, pH 6.2 | 307.0 ± 1.7 |
| P62ProT | 10 mM sodium phosphate, 3% (w/v) proline, 0.03% (w/v) polysorbate 80, pH 6.2 | 294.0 ± 0.0 |

Materials. The VEGF-specific aflibercept fusion protein antagonist was produced using industry standard recombinant expression technology and purification processes. The purified drug substance was buffer exchanged against the specified formulation buffers using either a lab scale or a bench scale tangential flow filtration system by Millipore Corporation. Protein concentrations were adjusted to the final target concentration by diluting with formulation buffer. The water used in making all formulations was purified by a Milli-Q® (Millipore Corporation) water purification system, which includes an ion exchange cartridge. The purity of the water was monitored by measuring the conductivity, with a value greater than 18.2 MΩ cm-1 (@ 25 Å° C.) being acceptable. All excipients, buffers and other ingredients used for the preparation of formulation buffers were USP grade or equivalent.

Methods.

Titrations. Acid and base conjugates, prepared at equal molarity, were blended together at the appropriate molar ratios to achieve the desired formulation pH for the histidine and phosphate buffer systems. The acetate formulations were prepared using the conjugate method or by using a glacial acetic acid addition to Milli-Q-purified water followed by a sodium hydroxide titration to reach the desired final pH.

Mass Spectrometry Based Multi-Attribute Method (MAM).

Stability samples were denatured with 6.8 M guanidine, reduced with 10 mM Dithiothreitol (DTT), and alkylated with 20 mM iodoacetic acid. Excess reagents were removed by size-exclusion based desalting columns. Trypsin was added at a 1:10 enzyme to substrate ratio and samples were digested for 30 minutes at 37° C. The resulting peptides were separated by RP-HPLC with a formic acid/acetonitrile (FA/ACN) gradient over a C18 column and monitored by mass spectrometry detection using a Thermo Fisher Q-Exactive Mass Spectrometer. Identification and quantification of the individual peptides was performed using Genedata's Expressionist software.

Other analytic methods were performed as described above in Example 1.

Figure 11:
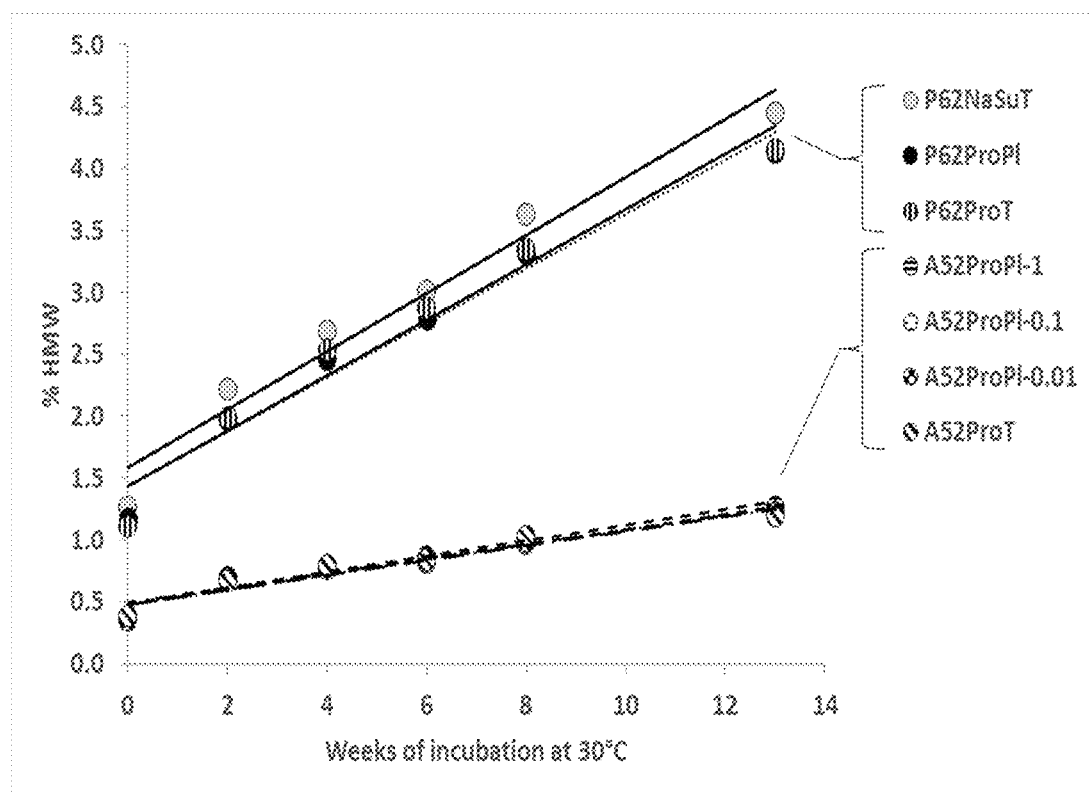
FIG. 11 shows HMW formation in various aflibercept formulations stored at 30° C., as measured by SE-HPLC. (See, Table 4 for formulation abbreviations.)
Figure 12:
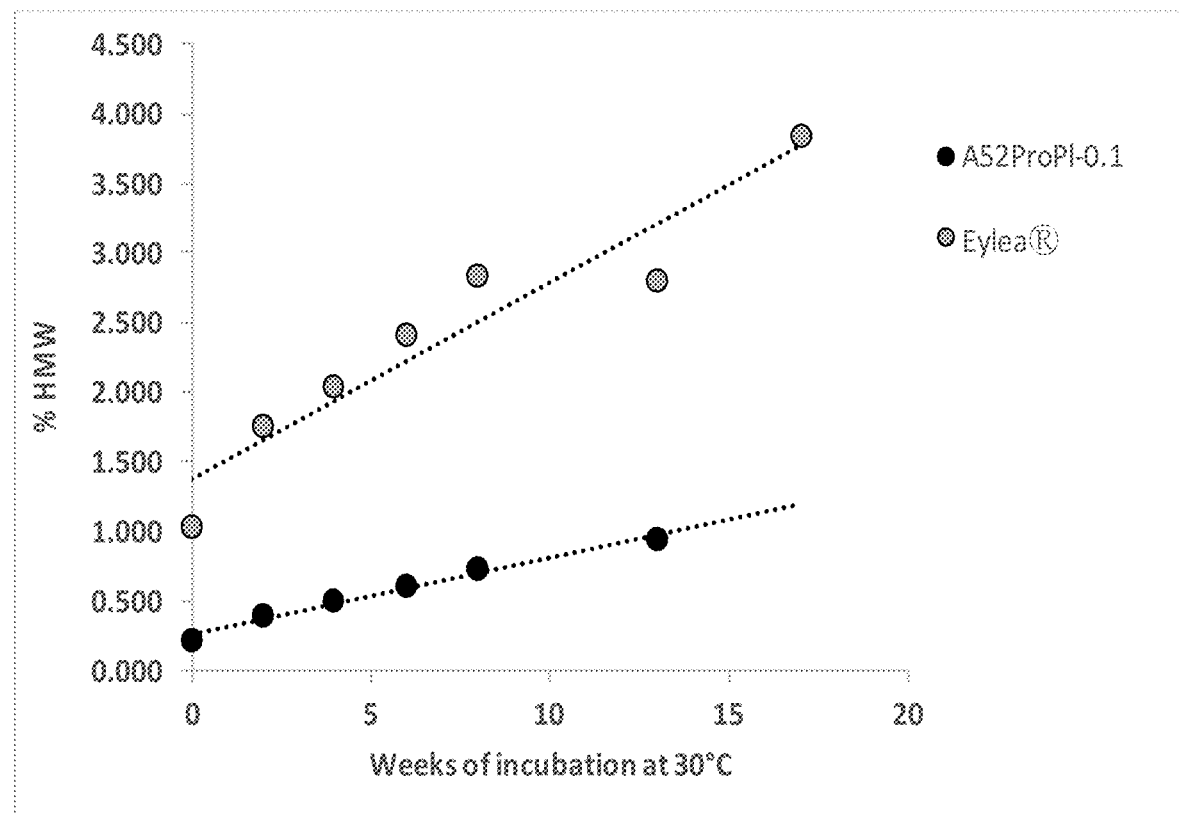
FIG. 12 shows results of a stability comparison of recombinantly produced aflibercept at 30° C. compared to commercially obtained Eylea® (aflibercept; Regeneron Pharmaceuticals, Inc., Tarrytown, N.Y.). The recombinantly produced aflibercept was made by Just Biotherapeutics (Seattle, WA) and formulated in 10 mM acetate, 3% (w/v) proline, pH 5.2, 0.1% (w/v) poloxamer formulation (A52ProP1-0.1).
Figure 13:
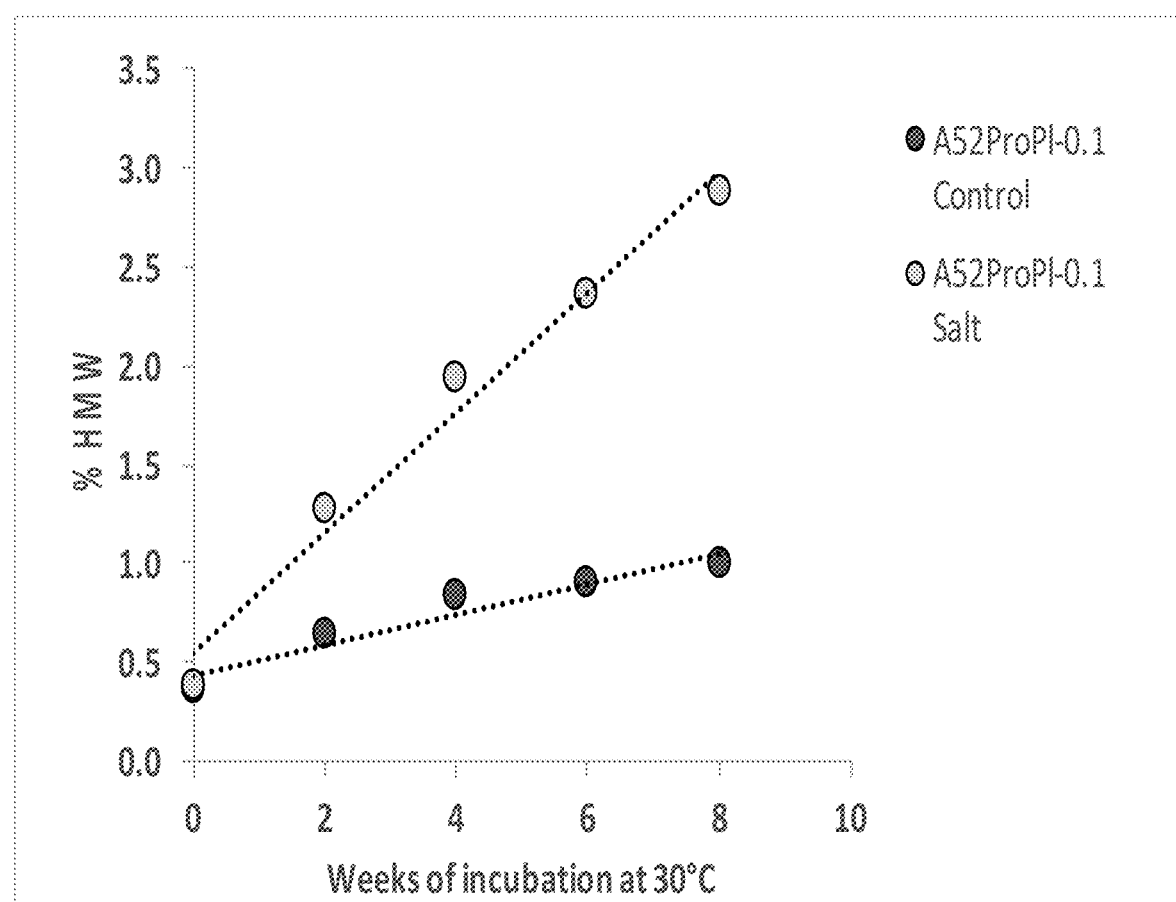
FIG. 13 illustrates the effect of 100 mM sodium chloride ("salt"), compared to a control (minus any added sodium chloride), on the stability of recombinantly produced aflibercept in 10 mM acetate, 3% (w/v) proline, pH 5.2 formulation (A52ProP1-0.1), during storage at 30° C.

Effect of pH on the Stability of Aflibercept. The effect of pH on the rate of high molecular weight formation as measured by SE-HPLC at 4° C. and 30° C. (see, FIG. 11) and sub-visible particle formation as measured by HIAC at 4° C. was examined using aflibercept produced recombinantly in three (3) different lots, at varying productions scales. Aflibercept produced at the three different scales showed similar product characteristics including similar levels of glycosylation across all lots. The aflibercept was then formulated with 10 mM acetate, 3% (w/v) proline and 0.1% (w/v) poloxamer 188 to three (3) different pH values (see, Table 4 for formulation abbreviations). As shown in Table 5 and Table 6 and FIG. 11, the rate of SE-HPLC-measured HMW formation of aflibercept formulated in 10 mM acetate, 3% (w/v) proline and 0.1% (w/v) poloxamer 188 was not affected by pH and was consistently lower than the rates of change observed for the same lots of aflibercept formulated in 10 mM sodium phosphate, 40 mM sodium chloride, 5% (w/v) sucrose and 0.03% (w/v) polysorbate 20, pH 6.2. Sub-visible particle formation measured by HIAC was also examined during storage at 4° C. and did not significantly change for aflibercept in any formulations during the storage period (Table 7).

TABLE 5

Rate of HMW formation at 4° C. as measured by SE-HPLC;

| | | % High Molecular Weight (HMW) formation at 4° C. | | | | | | Rate of Change |
|---|---|---|---|---|---|---|---|---|
| Lot | Formulation | 0 weeks | 2 weeks | 4 weeks | 6 weeks | 8 weeks | 13 weeks | (% HMW per week) |
| 2 | P62NaSuT | 0.69 | | 1.54 | | 1.72 | 1.95 | 0.090 |
| 2 | A52ProPl-0.1 (pH 5.0)* | 0.31 | | 0.42 | | 0.43 | 0.49 | 0.012 |
| 3 | P62NaSuT | 1.18 | 1.45 | 1.56 | 1.56 | 1.70 | 1.96 | 0.055 |
| 3 | A52ProPl-0.1 (pH 5.3)* | 0.35 | 0.44 | 0.47 | 0.51 | 0.54 | 0.64 | 0.021 |
| 1 | P62NaSuT | 0.33 | | 0.49 | | 0.60 | 0.66 | 0.025 |
| 1 | A52ProPl-0.1 (pH 5.6)* | 0.22 | | 0.24 | | 0.32 | 0.37 | 0.012 |

*The value in parenthesis refers to the measured pH of the solution.

TABLE 6

Rate of HMW formation at 30° C. as measured by SE-HPLC;

| | | % High Molecular Weight (HMW) formation at 30° C. | | | | | | Rate of Change |
|---|---|---|---|---|---|---|---|---|
| Lot | Formulation | 0 weeks | 2 weeks | 4 weeks | 6 weeks | 8 weeks | 13 weeks | (% HMW per week) |
| 2 | P62NaSuT | 0.69 | 2.44 | 3.39 | 3.91 | 4.63 | 5.97 | 0.467 |
| 2 | A52ProPl-0.1 (pH 5.0)* | 0.31 | 0.56 | 0.71 | 0.80 | 0.95 | 1.49 | 0.076 |
| 3 | P62NaSuT | 1.18 | 2.24 | 2.84 | 3.14 | 3.64 | 4.58 | 0.246 |
| 3 | A52ProPl-0.1 (pH 5.3)* | 0.35 | 0.69 | 0.81 | 0.86 | 0.96 | 1.22 | 0.060 |
| 1 | P62NaSuT | 0.33 | 0.94 | 1.31 | 1.73 | 2.18 | 3.39 | 0.225 |
| 1 | A52ProPl-0.1 (pH 5.6)* | 0.22 | 0.39 | 0.51 | 0.61 | 0.73 | 0.95 | 0.062 |

*The value in parenthesis refers to the measured pH of the solution.

TABLE 7

Subvisible particle formation at 4° C. as measured by small volume HIAC analysis;

| | | Sub-visible particle formation at 4° C. (values are cumulative counts ≥10 μm) | | | | | |
|---|---|---|---|---|---|---|---|
| Lot | Formulation | 0 weeks | 2 weeks | 4 weeks | 6 weeks | 8 weeks | 13 weeks |
| 2 | P62NaSuT | 20.00 | | 13.33 | | 15.00 | 20.00 |
| 2 | A52ProPl-0.1 (pH 5.0)* | 20.00 | | 11.67 | | 10.00 | 3.33 |
| 3 | P62NaSuT | 16.67 | 13.33 | 13.33 | 10.00 | 8.33 | 26.67 |
| 3 | A52ProPl-0.1 (pH 5.3)* | 3.33 | 3.33 | 10.00 | 8.33 | 6.67 | 15.00 |
| 1 | P62NaSuT | 10.00 | | 10.00 | | 13.33 | 15.00 |
| 1 | A52ProPl-0.1 (pH 5.6)* | 48.33 | | 11.67 | | 8.33 | 21.67 |

*The value in parenthesis refers to the measured pH of the solution.

Stability of Aflibercept in Proline and Arginine Formulations Containing Different Non-Ionic Surfactants. The stability of aflibercept in a formulation containing either proline or arginine as a tonicifying agent was examined in the presence of either of two surfactants, poloxamer 188 or polysorbate 80 (Table 8 and Table 9, respectively; see, Table 4 for formulation abbreviations). HMW species formation as measured by SE-HPLC at 30° C. was significantly reduced when aflibercept was formulated in 10 mM acetate, 3% (w/v) proline, pH 5.2, as compared to 10 mM sodium phosphate, 40 mM sodium chloride, 5% (w/v) sucrose, pH 6.2, when each was formulated with either polysorbate 80 or Poloxamer 188. Aflibercept in the 10 mM phosphate, 3% (w/v) proline, pH 6.2, showed a similar rate of SE-HPLC-measured HMW formation to that of aflibercept in the 10 mM sodium phosphate, 40 mM sodium chloride, 5% (w/v) sucrose, pH 6.2 formulation (each formulated with either polysorbate 80 or Poloxamer 188, as non-ionic surfactant). In contrast, replacement of the proline with arginine as the tonicifying agent in the acetate formulation at pH 5.2 increased the rate of SE-HPLC-measured HMW formation by at least 10-fold. However, in the 10 mM phosphate buffer, pH 6.2 formulation the arginine showed similar stability to the aflibercept in the 10 mM phosphate, 3% (w/v) proline, pH 6.2 formulation, regardless of which type of non-ionic surfactant was present.

TABLE 8

Rate of HMW formation at 30° C. as measured by SE-HPLC. Poloxamer 188 (0.1% (w/v)) was present as the non-ionic surfactant in each formulation tested.

| | % High Molecular Weight (HMW) formation at 30° C. | | | | | | | Rate of Change (% HMW/week) |
|---|---|---|---|---|---|---|---|---|
| Formulation | 0 weeks | 2 weeks | 4 weeks | 6 weeks | 8 weeks | 10 weeks | 12 weeks | |
| A52ProPl-0.1 | 0.42 | 0.57 | 0.71 | 0.82 | 0.91 | 0.94 | 0.97 | 0.05 |
| A52ArgPl-0.1 | 0.37 | 1.13 | 2.32 | 3.31 | 4.40 | 5.68 | 7.05 | 0.56 |
| P62ProPl-0.1 | 0.60 | 1.15 | 1.42 | 1.90 | 2.20 | 2.38 | 2.54 | 0.16 |
| P62ArgPl-0.1 | 0.48 | 0.90 | 1.29 | 1.74 | 1.99 | 2.38 | 2.78 | 0.19 |
| P62NaSuPl-0.1 | 0.61 | 1.10 | 1.36 | 1.82 | 2.11 | 2.21 | 2.38 | 0.15 |

TABLE 9

Rate of HMW formation at 30° C. as measured by SE-HPLC. Polysorbate 80 (0.03% (w/v)) was present as the non-ionic surfactant in each formulation tested.

| | % High Molecular Weight (HMW) formation at 30° C. | | | | | | | Rate of Change (% HMW/week) |
|---|---|---|---|---|---|---|---|---|
| Formulation | 0 weeks | 2 weeks | 4 weeks | 6 weeks | 8 weeks | 10 weeks | 12 weeks | |
| A52ProT | 0.44 | 0.56 | 0.72 | 0.84 | 0.94 | 1.04 | 1.11 | 0.06 |
| A52ArgT | 0.39 | 1.58 | 4.24 | 6.76 | 9.23 | 11.24 | 13.77 | 1.15 |
| P62ProT | 0.60 | 1.11 | 1.44 | 1.88 | 2.10 | 2.35 | 2.61 | 0.16 |
| P62ArgT | 0.45 | 0.90 | 1.30 | 1.78 | 1.99 | 2.42 | 2.82 | 0.19 |
| P62NaSuT | 0.60 | 1.08 | 1.40 | 1.79 | 1.88 | 2.25 | 2.32 | 0.14 |

Stability of Aflibercept Following Simulated Shipping and Effect of Surfactant Concentration. The stability of aflibercept was characterized in the 10 mM acetate, 3% (w/v) proline, pH 5.2 formulation with various surfactants and concentrations following simulated shipping. The simulated shipping protocol was designed to account for multiple modes of transportation that could potentially damage the product and affect the stability profile. As shown in Table 10, the rate of SE-HPLC-measured HMW formation of aflibercept stored at 4° C. in the 10 mM acetate, 3% (w/v) proline, pH 5.2 formulation was not dependent on the type of surfactant or the concentration of surfactant, and was significantly less than that observed for the aflibercept in the 10 mM phosphate, 40 mM sodium chloride, 5% (w/v) sucrose, pH 6.2 formulation. In line with prior results, the aflibercept stability in the 10 mM phosphate, 3% (w/v) proline, pH 6.2 was similar to that in the 10 mM phosphate, 40 mM sodium chloride, 5% (w/v) sucrose, pH 6.2 formulation. Additionally, while the rate of HMW formation at 30° C. was faster than that at 4° C., the order of stability did not change, with the 10 mM acetate, 3% (w/v) proline, pH 5.2 being the most stable (Table 11). Following the simulated shipping, the sub-visible particle counts measured by HIAC increased to a similar degree across all formulations (Table 12, compare columns for 0 weeks control to 0 weeks). The sub-visible particle counts measured by HIAC did not appear to be dependent on formulation. Product potency was assessed at the 13-week time point for a subset of formulations and storage temperatures (see, Table 13). No differences in potency were detected between the 10 mM acetate, 3% (w/v) proline, pH 5.2 formulations or the 10 mM phosphate, 3% (w/v) proline, pH 6.2, when compared with the 10 mM phosphate, 40 mM sodium chloride, 5% (w/v) sucrose, pH 6.2 formulation. These results indicate the various proline formulations stabilize the protein and maintain functional activity.

Mass Spectrometry Based Multi-Attribute Method (MAM) Analysis. MAM analysis was conducted to evaluate the change in post translational modification levels for attributes such as isomerization of aspartic acid residues, deamidation of asparagine, and oxidation of methionine. Samples from three formulations were evaluated after 3 months of storage at 4° C., 30° C. and 40° C. compared to a −70° C. control sample. In this analysis, the 10 mM acetate, 3% (w/v) proline, 0.1% (w/v) poloxamer 188, pH 5.2 and the 10 mM acetate, 3% (w/v) proline, 0.03% (w/v) polysorbate 80, pH 5.2 were compared with the aflibercept commercial formulation 10 mM sodium phosphate, 40 mM sodium chloride, 5% (w/v) sucrose, 0.03% (w/v) polysorbate 20, pH 6.2.

Equivalent levels of methionine oxidation were observed between the −70° C. control and the 4° C. stability samples for the three formulations. Higher levels of oxidation were observed in all three formulations after 30° C. and 40° C. storage, with the lowest level of oxidation reported for the 10 mM acetate, 3% (w/v) proline, 0.1% (w/v) poloxamer 188, pH 5.2. The two formulations with higher levels of methionine oxidation, contained polysorbate, an excipient known to promote oxidation of proteins (Kerwin, *Polysorbates 20 and 80 Used in the Formulation of Protein Biotherapeutics: Structure and Degradation Pathways*, Journal of Pharmaceutical Sciences, (2008) 97, 8:2924-2934).

The deamidation levels were assessed for the three formulations after 3 months of 4° C., 30° C. and 40° C. storage. No detectable differences were observed between the 4° C. samples however samples stored at the elevated temperatures, had significant increases in deamidation levels. For example, the 40° C. aflibercept formulation (10 mM sodium phosphate, 40 mM sodium chloride, 5% (w/v) sucrose, 0.03% (w/v) polysorbate 20, pH 6.2.) had 7.6% deamidation on position N84, whereas the 10 mM acetate, 3% (w/v) proline, 0.1% (w/v) poloxamer 188, pH 5.2 and the 10 mM acetate, 3% (w/v) proline, 0.03% (w/v) polysorbate 80, pH 5.2 formulations had 2.8% and 3.0% N84 deamidation, respectively. Across all five detected deamidation sites, the 10 mM acetate, 3% (w/v) proline, pH 5.2 formulations had significantly lower deamidation after elevated temperatures storage than the phosphate formulation at pH 6.2.

The level of isomerized aspartic acid residues was also evaluated during the MAM analysis. Six (6) aspartic residues were susceptible to isomerization. Regardless of temperature or formulation, the measured differences in % isomerization levels were within the error of the measurement technique, therefore conclusions could not be drawn from these data.

In summary, the MAM data indicate the 10 mM acetate, 3% (w/v) proline, 0.1% (w/v) poloxamer 188, pH 5.2 formulation had a lower or equivalent rate of post-translational modification formation than the commercial aflibercept formulation 10 mM sodium phosphate, 40 mM sodium chloride, 5% (w/v) sucrose, 0.03% (w/v) polysorbate 20, pH 6.2.

TABLE 10

Rate of HMW formation at 4° C. as measured by SE-HPLC;

| Formulation | % High Molecular Weight (HMW) formation at 4° C. | | | | | | | Rate of Change |
|---|---|---|---|---|---|---|---|---|
| | 0 weeks control* | 0 weeks | 2 weeks | 4 weeks | 6 weeks | 8 weeks | 13 weeks | (% HMW/ week) |
| P62NaSuT | 1.18 | 1.27 | 1.48 | 1.48 | 1.48 | 1.81 | 1.96 | 0.052 |
| A52ProPl-1 | 0.37 | 0.37 | 0.47 | 0.48 | 0.48 | 0.61 | 0.67 | 0.022 |
| A52ProPl-0.1 | 0.35 | 0.37 | 0.44 | 0.43 | 0.46 | 0.56 | 0.63 | 0.020 |
| A52ProPl-0.01 | 0.33 | 0.35 | 0.43 | 0.43 | 0.47 | 0.56 | 0.63 | 0.021 |
| A52ProT | 0.35 | 0.39 | 0.44 | 0.44 | 0.46 | 0.55 | 0.60 | 0.017 |
| P62ProPl-0.1 | 1.06 | 1.18 | 1.30 | 1.34 | 1.36 | 1.64 | 1.76 | 0.046 |
| P62ProT | 1.09 | 1.11 | 1.27 | 1.32 | 1.33 | 1.56 | 1.74 | 0.047 |

*Control refers to material that was held at 4° C. during the shipping studies without undergoing the simulated transport treatment. (See, Table 4 for formulation abbreviations.)

TABLE 11

Rate of HMW formation at 30° C. as measured by SE-HPLC;

| Formulation | % High Molecular Weight (HMW) formation at 30° C. | | | | | | | Rate of Change |
|---|---|---|---|---|---|---|---|---|
| | 0 weeks control* | 0 weeks | 2 weeks | 4 weeks | 6 weeks | 8 weeks | 13 weeks | (% HMW/ week) |
| P62NaSuT | 1.18 | 1.27 | 2.22 | 2.69 | 3.01 | 3.63 | 4.45 | 0.234 |
| A52ProPl-1 | 0.37 | 0.37 | 0.70 | 0.78 | 0.86 | 1.02 | 1.27 | 0.064 |
| A52ProPl-0.1 | 0.35 | 0.37 | 0.68 | 0.77 | 0.82 | 0.97 | 1.22 | 0.059 |
| A52ProPl-0.01 | 0.33 | 0.35 | 0.68 | 0.78 | 0.84 | 0.99 | 1.22 | 0.061 |
| A52ProT | 0.35 | 0.39 | 0.67 | 0.79 | 0.84 | 1.03 | 1.2 | 0.059 |
| P62ProPl-0.1 | 1.06 | 1.18 | 1.98 | 2.46 | 2.79 | 3.31 | 4.14 | 0.220 |
| P62ProT | 1.09 | 1.11 | 1.99 | 2.54 | 2.87 | 3.35 | 4.15 | 0.224 |

*Control refers to material that was held at 4° C. during the shipping studies without undergoing the simulated transport treatment. (See, Table 4 for formulation abbreviations.)

TABLE 12

Rate of sub-visible particle formation at 4° C. as measured by HIAC:

| | Sub-visible particle formation at 4° C. (values are cumulative counts ≥ 10 μm) | | | | | |
|---|---|---|---|---|---|---|
| | 0 weeks control* | 0 weeks | 2 weeks | 4 weeks | 6 weeks | 8 weeks | 13 weeks |
| P62NaSuT | 16.67 | 20.00 | 11.67 | 23.33 | 25.00 | 20.00 | 15.00 |
| A52ProPl-1 | 3.33 | 30.00 | 23.33 | 20.00 | 48.33 | 18.33 | 21.67 |
| A52ProPl-0.1 | 3.33 | 40.00 | 15.00 | 16.67 | 28.33 | 8.33 | 10.00 |
| A52ProPl-0.01 | 3.33 | 25.00 | 20.00 | 11.67 | 45.00 | 8.33 | 13.33 |
| A52ProT | 5.00 | 8.33 | 16.67 | 15.00 | 13.33 | 3.33 | 11.67 |
| P62ProPl-0.1 | 8.33 | 28.33 | 40.00 | 50.00 | 31.67 | 30.00 | 10.00 |
| P62ProT | 13.33 | 18.33 | 40.00 | 11.67 | 13.33 | 11.67 | 5.00 |

*Control refers to material that was held at 4° C. during the shipping studies without undergoing the simulated transport treatment. (See, Table 4 for formulation abbreviations).

TABLE 13

Relative Potency:

| | % Relative Potency—13-week Time Point | | | | | |
|---|---|---|---|---|---|---|
| | −70° C. | SD | 4° C. | SD | 30° C. | SD |
| P62NaSuT | 98.8 | 8.4 | 101.2 | 2.5 | NT* | |
| A52ProPl-0.1 | 95.5 | 4.2 | 101.2 | 3.2 | 95.1 | 2.5 |
| A52ProPl-0.01 | NT* | | 115.8 | 13.7 | NT* | |
| A52ProT | NT* | | 105.0 | 5.9 | 94.0 | 10.1 |
| P62ProPl-0.1 | 93.8 | 14.1 | 94.6 | 6.2 | NT* | |
| P62ProT | NT* | | 93.5 | 6.9 | NT* | |

*NT—All temperatures were not tested by the potency assay; otherwise n = 3.

Comparison of Recombinantly Produced Aflibercept in an Inventive Acetate-Buffered Formulation Compared to Commercially Obtained Eylea®. The stability of recombinantly produced aflibercept at 30° C. in the 10 mM acetate, 3% (w/v) proline, pH 5.2, 0.1% (w/v) poloxamer formulation was compared to that of Eylea® (aflibercept; Regeneron Pharmaceuticals, Inc., Tarrytown, N.Y.; see, Table 14). Unless particularly noted herein as being commercially obtained, aflibercept used in all experiments described herein was produced recombinantly for these studies by Just Biotherapeutics, Inc. (Seattle, WA) and was formulated in the formulations described in Table 1 and Table 4 herein. Eylea® drug product was purchased from the European market and placed on stability in its own container. Samples were removed from the vial at the indicated time points and analyzed by SE-HPLC to characterize the amount of HMW species present. The data in Table 14 demonstrate that aflibercept produced by Just Biotherapeutics and formulated in the indicated formulation had lower % HMW and a lower rate of HMW species formation than aflibercept in the Eylea® drug product.

TABLE 14

Comparison of the rate of HMW formation (SE-HPLC) at 30° C. for an embodiment of the inventive formulation and a commercially obtained aflibercept formulation (Eylea ®).

| | % High Molecular Weight (HMW) formation at 30° C. (after indicated number of weeks) | | | | | | | | Rate of Change (% HMW/week) |
|---|---|---|---|---|---|---|---|---|---|
| Formulation | 0 | 2 | 4 | 6 | 8 | 13 | 17 | 21 | |
| A52ProPl-0.1 | 0.22 | 0.39 | 0.51 | 0.61 | 0.73 | 0.95 | — | — | 0.055 |
| Eylea ® | 1.03 | 1.74 | 2.03 | 2.41 | 2.83 | 2.79 | 3.84 | 4.85 | 0.172 |

(See, Table 4 for formulation abbreviations.)

Effect of Salt on the Stability of Aflibercept Formulation. The effect of salt on the stability of aflibercept was investigated in the 10 mM acetate, 3% (w/v) proline, pH 5.2 formulation during storage at 30° C. As shown in Table 15, the addition of 100 mM sodium chloride salt to the formulation increased the rate of SE-HPLC-measured HMW species formation by 3.8-fold.

TABLE 15

Comparison of the rate of HMW formation (SE-HPLC) at 30° C. for an embodiment of the inventive formulation with or without 100 mM sodium chloride salt

| Formulation | % High Molecular Weight (HMW) formation at 30° C. | | | | | Rate of Change (% HMW/ Week) |
|---|---|---|---|---|---|---|
| | 0 weeks | 2 weeks | 4 weeks | 6 weeks | 8 weeks | |
| A52ProPl-0.1 (Control) | 0.37 | 0.63 | 0.83 | 0.90 | 0.99 | 0.076 |
| A52ProPl-0.1, 100 mM sodium chloride | 0.38 | 1.28 | 1.93 | 2.36 | 2.87 | 0.303 |

Stability Comparison of Commercially Obtained Aflibercept with Recombinant Aflibercept Used in these Experiments. Aflibercept, purchased commercially as Zaltrap®, (ziv-aflibercept; Regeneron Pharmaceuticals, Inc., Tarrytown, N.Y.) was reprocessed to remove the commercial formulation components (other than ziv-aflibercept), and reformulated into the 10 mM phosphate, 40 mM sodium chloride, 5% (w/v) sucrose, 0.03% (w/v) polysorbate 20, pH 6.2 formulation (P62NaSuT). The commercially obtained reprocessed aflibercept and recombinant aflibercept, produced for these studies by Just Biotherapeutics, Inc. and formulated in 10 mM phosphate, 40 mM sodium chloride, 5% (w/v) sucrose, 0.03% (w/v) polysorbate 20, pH 6.2, were incubated at 30° C. and the HMW formation was monitored. As shown in Table 16, the rate of HMW formation of the aflibercept purified from commercially obtained Zaltrap® was slightly faster than that observed for aflibercept produced by Just Biotherapeutics. These results demonstrate that there was not a substantial difference in the inherent aggregation rate of aflibercept fusion proteins obtained commercially compared to aflibercept protein used in the experiments described herein.

TABLE 16

HMW formation (SE-HPLC) at 30° C. of commercially obtained ziv-aflibercept (Zaltrap®) compared with recombinantly produced aflibercept (by Just Biotherapeutics, Inc.).

| Formulation | % High Molecular Weight (HMW) formation at 30° C. | | | | | Rate of Change (% HMW/ Week) |
|---|---|---|---|---|---|---|
| | 0 weeks | 2 weeks | 4 weeks | 6 weeks | 8 weeks | |
| in P62NaSuT Aflibercept: commercially obtained and reformulated | 2.08 | 2.34 | 2.94 | 3.84 | 4.26 | 0.29 |
| Aflibercept: recombinantly produced | 0.60 | 1.24 | 1.61 | — | 2.33 | 0.21 |

Example 4. Tolerability Study of Multiple Placebo Formulations by Intravitreal Administration in Rabbits To determine the tolerability of some embodiments of the inventive formulations intended for use with an aflibercept drug product, intravitreal injections of placebo formulations were administered as a single dose to rabbits, at Charles River Laboratories, Inc., 640 N. Elizabeth Street, Spencerville, OH 45887, United States of America, as shown in Table 17.

TABLE 17

Placebo formulations tested as a single dose in male rabbits.

| Group No. | Test Material | Dose Volume (mL) | Number of animals (Males) |
|---|---|---|---|
| 1 | Placebo 1 (10 mM Phosphate, 40 mM NaCl, 5% (w/v) Sucrose, 0.03% (w/v) polysorbate 20, pH 6.2) | 0.05 | 3 |
| 2 | Placebo 2 (10 mM Acetate, 3% (w/v) Proline, 0.1% (w/v) poloxamer 188, pH 5.2) | 0.05 | 3 |
| 3 | Placebo 3 (10 mM Acetate, 3% (w/v) Proline, 0.03% (w/v) polysorbate 80, pH 5.2) | 0.05 | 3 |
| 4 | Placebo 4 (10 mM Phosphate, 3% (w/v) Proline, 0.1% (w/v) poloxamer 188, pH 6.2) | 0.05 | 3 |
| 5 | Placebo 5 (10 mM Phosphate, 3% (w/v) Proline, 0.03% (w/v) polysorbate 80, pH 6.2) | 0.05 | 3 |

The following parameters and end points were evaluated as per the study design: clinical signs, body weights, body weight gains, food consumption, and ophthalmology.

Among the subject rabbits in the study, there were no early deaths, no treatment-related clinical signs, and no effects on body weight, body weight gain, food consumption, nor any ophthalmic findings. In conclusion, administration of all placebo formulations by intravitreal injection was well tolerated in rabbits.

We claim:

1. An ophthalmic formulation, comprising:
   (a) aflibercept in a concentration of 5-100 mg/mL;
   (b) a histidine buffer, wherein the histidine buffer concentration is 5-50 mM;
   (c) a non-ionic surfactant selected from the group consisting of a polysorbate, a polyethylene glycol dodecyl ether, a poloxamer, 4-(1,1,3,3-Tetramethylbutyl)phenyl-polyethylene glycol, an alkylsaccharide and an alkylglycoside, at a concentration of 0.001% (w/v) to 5% (w/v);
   (d) a tonicifying agent comprising a polyol or an amino acid selected from proline, arginine, aspartate, glutamate, glycine, histidine, isoleucine, and lysine, at a concentration of 2-4% (w/v), wherein the formulation has a final osmolality of 300±50 mOsm/kg;
   (e) an additional amino acid stabilizing agent selected from the group consisting of proline, arginine, methionine, lysine and mixtures thereof; and
   wherein the pH of the formulation is about pH 5.0 to about pH 6.5.

2. The ophthalmic formulation of claim 1, wherein the histidine buffer concentration is 5-20 mM.

3. The ophthalmic formulation of claim 1, wherein the non-ionic surfactant is a polysorbate or Poloxamer 188.

4. The ophthalmic formulation of claim 1, wherein the tonicifying agent is a polyol selected from sucrose, trehalose, sorbitol, mannitol, and glycerol.

5. The ophthalmic formulation of claim 1, wherein the tonicifying agent is sucrose.

6. The ophthalmic formulation of claim 1, wherein the tonicifying agent is trehalose.

7. The ophthalmic formulation of claim 1, wherein the tonicifying agent is an amino acid selected from proline, arginine, aspartate, glutamate, histidine, isoleucine, and lysine.

8. The ophthalmic formulation of claim 1, wherein the tonicifying agent is proline.

9. The ophthalmic formulation of claim 1, wherein the tonicifying agent is arginine.

10. The ophthalmic formulation of claim 1, wherein:
    (i) the non-ionic surfactant is polysorbate or poloxamer;
    (ii) the tonicifying agent is sucrose or trehalose;
    (iii) the additional amino acid stabilizing agent is proline, arginine, or lysine; and
    the pH of the formulation is about pH 5.5 to about pH 6.5.

11. The ophthalmic formulation of claim 10, wherein the non-ionic surfactant is a poloxamer.

12. The ophthalmic formulation of claim 1, wherein the aflibercept concentration is 20-80 mg/mL.

13. The ophthalmic formulation of claim 1, wherein the aflibercept concentration is at about 30 mg/mL to about 50 mg/mL.

14. A method of treating an eye disorder or disease, comprising administering a therapeutically effective amount of the ophthalmic formulation of claim 1 by intravitreal injection to a patient in need of treatment, wherein the eye disorder or disease is selected from the group consisting of macular edema following Retinal Vein Occlusion (RVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD).

15. The method of claim 14, wherein the eye disorder or disease is macular edema following Retinal Vein Occlusion (RVO).

16. The method of claim 14, wherein the eye disorder or disease is Central Retinal Vein Occlusion (CRVO).

17. The method of claim 14, wherein the eye disorder or disease is Branch Retinal Vein Occlusion (BRVO).

18. The method of claim 14, wherein the eye disorder or disease is neovascular Age-Related Macular Degeneration (AMD) or Neovascular (Wet) Age-Related Macular Degeneration (AMD).

* * * * *

SEQUENCE LISTING

<160> NUMBER OF SEQ ID NOS: 1

<210> SEQ ID NO 1
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

```
Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
        370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
                420                 425                 430
```